(12) United States Patent
Awano et al.

(10) Patent No.: US 11,622,822 B2
(45) Date of Patent: Apr. 11, 2023

(54) SURGERY SUPPORTING APPARATUS FOR CONTROLLING MOTION OF ROBOT ARM, CONTROL METHOD OF THE SAME, AND NON-TRANSITORY COMPUTER-READABLE STORAGE MEDIUM

(71) Applicant: A-Traction Inc., Kashiwa (JP)

(72) Inventors: Keita Awano, Kashiwa (JP); Takehiro Ando, Kashiwa (JP); Hiroyuki Miyamoto, Kashiwa (JP); Yoshihide Sugiura, Kashiwa (JP); Yuta Fukushima, Kashiwa (JP)

(73) Assignee: A-TRACTION INC., Kashiwa (JP)

( * ) Notice: Subject to any disclaimer, the term of this patent is extended or adjusted under 35 U.S.C. 154(b) by 598 days.

(21) Appl. No.: 16/658,344

(22) Filed: Oct. 21, 2019

(65) Prior Publication Data

US 2020/0121403 A1    Apr. 23, 2020

(30) Foreign Application Priority Data

Oct. 23, 2018  (JP) .............................. JP2018-199386

(51) Int. Cl.
*A61B 34/00* (2016.01)
*A61B 34/30* (2016.01)
(Continued)

(52) U.S. Cl.
CPC .............. *A61B 34/30* (2016.02); *A61B 34/20* (2016.02); *B25J 9/1664* (2013.01);
(Continued)

(58) Field of Classification Search
CPC combination set(s) only.
See application file for complete search history.

(56) References Cited

U.S. PATENT DOCUMENTS

| 5,417,210 A | 5/1995 | Funda et al. |
| 9,554,827 B2 | 1/2017 | Omori |

(Continued)

FOREIGN PATENT DOCUMENTS

| CN | 104622585 A | 5/2015 |
| CN | 104736095 A | 6/2015 |

(Continued)

OTHER PUBLICATIONS

Office Action dated Jun. 14, 2019, issued in counterpart JP Application No. 2019-004439, with English translation (5 pages).

(Continued)

*Primary Examiner* — Richard G Louis
(74) *Attorney, Agent, or Firm* — Oliff PLC

(57) ABSTRACT

A surgery supporting apparatus is capable of controlling a posture of a first surgical instrument that is inserted into a body cavity and mechanically drivable, by using a second surgical instrument to be inserted into the body cavity. The apparatus comprises a robot arm configured to control the posture of the first surgical instrument attached to the robot arm. Instructions stored in a memory cause the apparatus to function as a control unit configured to control the motion of the robot arm such that the posture of the first surgical instrument is controlled in accordance with the posture of the second surgical instrument, in a case of a first mode, and controls the motion of the robot arm in accordance with a manipulation including contact to the robot arm, in a case of a second mode.

22 Claims, 18 Drawing Sheets

(51) Int. Cl.
*A61B 34/20* (2016.01)
*B25J 9/16* (2006.01)
*A61B 90/00* (2016.01)
*A61B 90/50* (2016.01)
*A61B 17/34* (2006.01)

(52) U.S. Cl.
CPC .......... *A61B 17/3423* (2013.01); *A61B 90/50* (2016.02); *A61B 2034/302* (2016.02); *A61B 2090/067* (2016.02)

(56) References Cited

U.S. PATENT DOCUMENTS

| | | | |
|---|---|---|---|
| 10,064,692 | B2 | 9/2018 | Nakanishi et al. |
| 2002/0055795 | A1 | 5/2002 | Niemeyer et al. |
| 2009/0082784 | A1 | 3/2009 | Meissner et al. |
| 2014/0052153 | A1* | 2/2014 | Griffiths ................ A61B 34/70 606/130 |
| 2014/0076077 | A1 | 3/2014 | Cooper et al. |
| 2016/0361125 | A1 | 12/2016 | Balicki et al. |
| 2017/0360520 | A1 | 12/2017 | Hares |
| 2019/0328469 | A1* | 10/2019 | Ando ..................... B25J 13/088 |

FOREIGN PATENT DOCUMENTS

| | | |
|---|---|---|
| CN | 108245253 A | 7/2018 |
| JP | 6-030896 A | 2/1994 |
| JP | 2005-118457 A | 5/2005 |
| JP | 2009-525098 A | 7/2009 |
| JP | 2011-4880 A | 1/2011 |
| JP | 2012-005557 A | 1/2012 |
| JP | 2013-526337 A | 6/2013 |
| JP | 2015-024025 A | 2/2015 |
| JP | 2017-104455 A | 6/2017 |
| JP | 6149175 B1 | 6/2017 |
| JP | 2018-110747 A | 7/2018 |
| WO | 00/07503 A1 | 2/2000 |
| WO | 2007/088208 A1 | 8/2007 |
| WO | 2011/143020 A1 | 11/2011 |
| WO | 2017/126101 A1 | 7/2017 |
| WO | 2018/131188 A1 | 7/2018 |
| WO | WO-2018131188 A1 * | 7/2018 ............. A61B 34/20 |

OTHER PUBLICATIONS

Office Action dated Dec. 14, 2018, issued in counterpart JP Application No. 2018-199386, with English translation (5 pages).
Office Action dated Jul. 1, 2019, issued in counterpart JP Application No. 2019-090054, with English translation (5 pages).
Extended European Search Report dated Feb. 3, 2020, issued in counterpart application No. 19204298.4. (16 pages).
Office Action dated Nov. 1, 2022, issued in counterpart CN application No. 201910992022.3, with English translation. (17 pages).

* cited by examiner

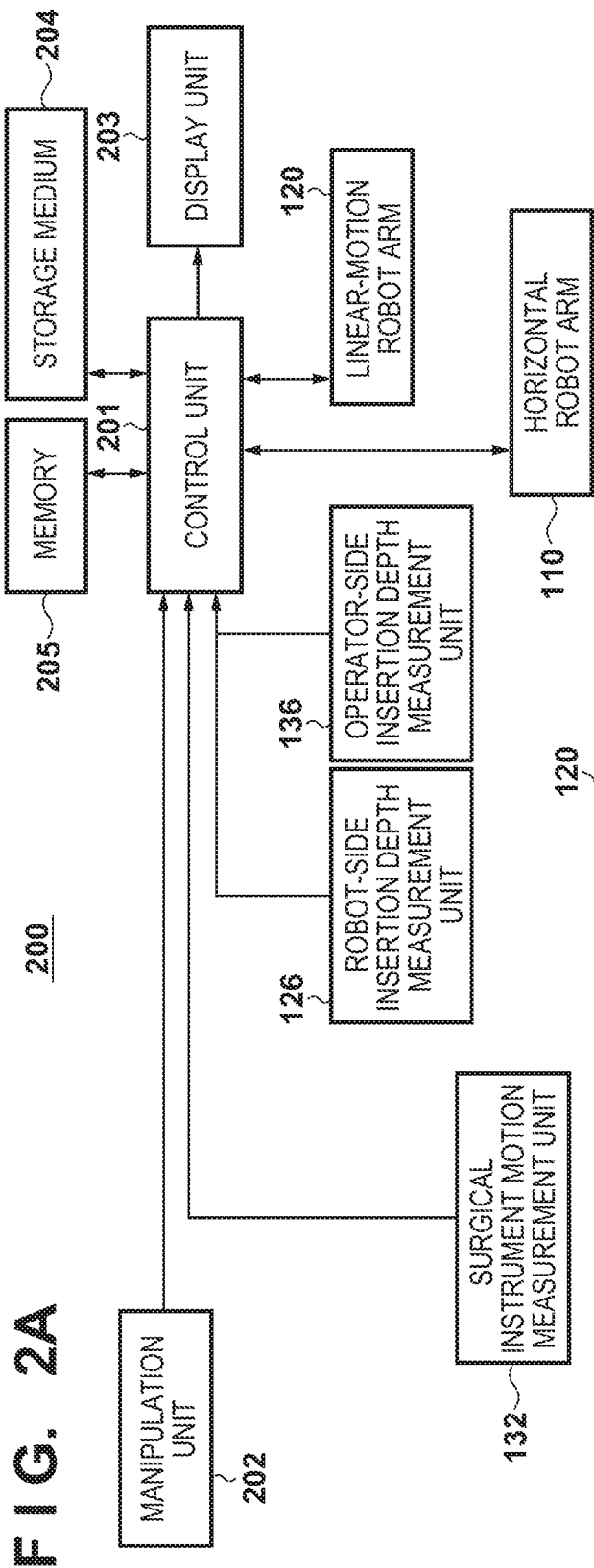
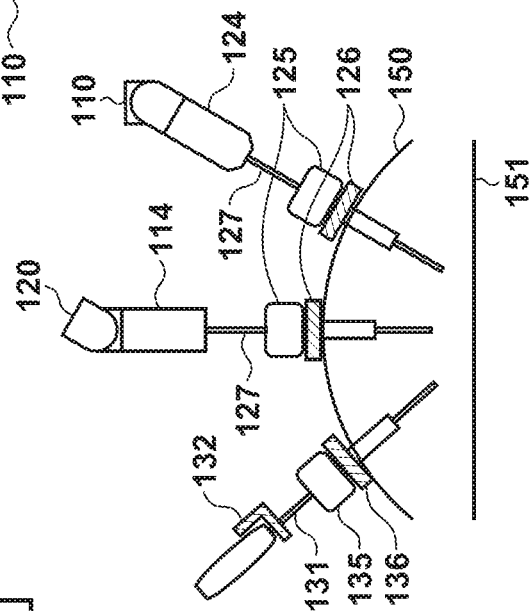
FIG. 2A
FIG. 2B

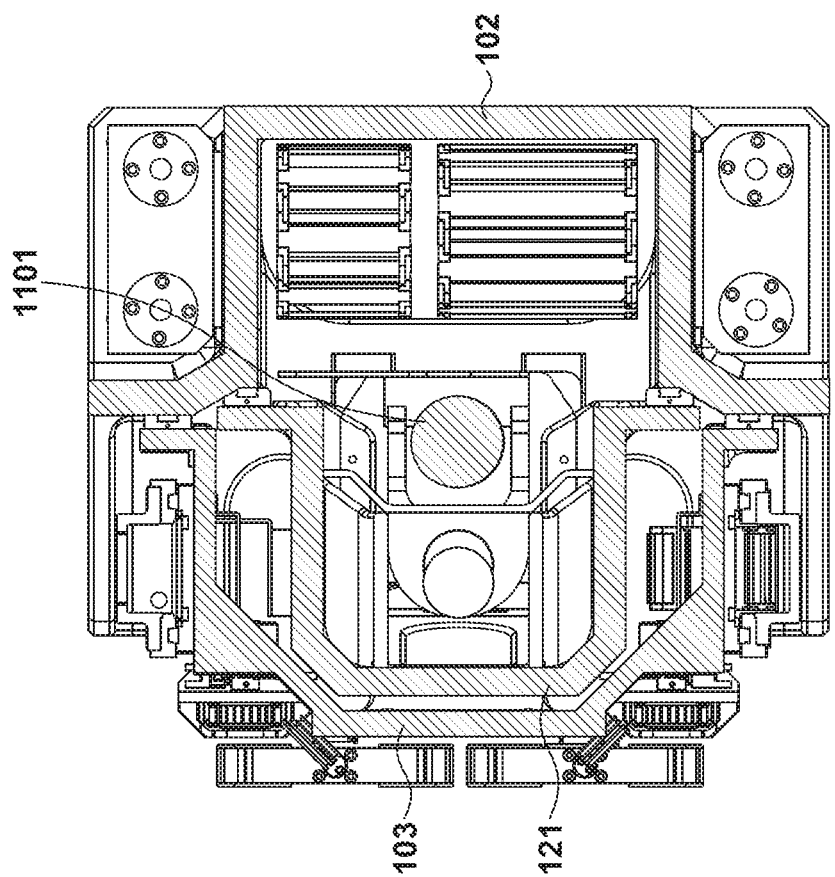
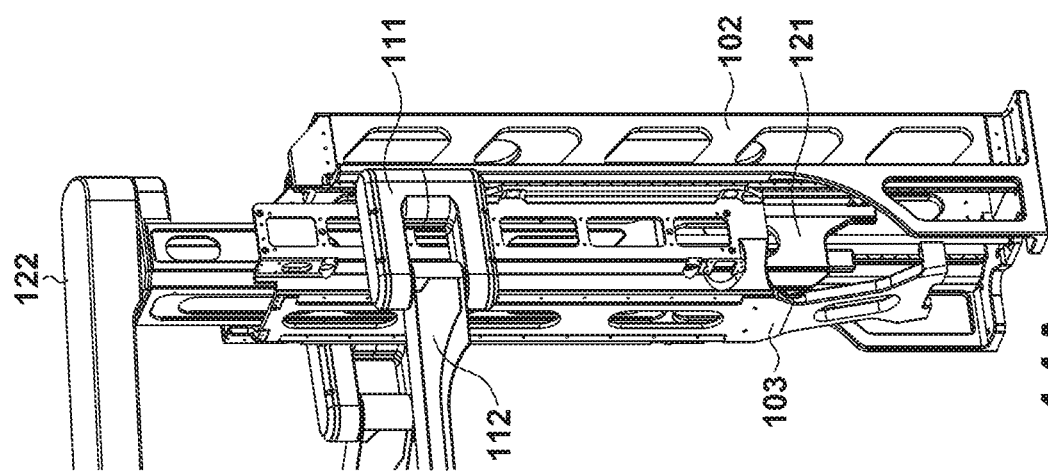

SURGERY SUPPORTING APPARATUS FOR CONTROLLING MOTION OF ROBOT ARM, CONTROL METHOD OF THE SAME, AND NON-TRANSITORY COMPUTER-READABLE STORAGE MEDIUM

CROSS-REFERENCE TO RELATED APPLICATION(S)

This application claims priority to and the benefit of Japanese Patent Application No. 2018-199386 filed on Oct. 23, 2019, the entire disclosure of which is incorporated herein by reference.

BACKGROUND OF THE INVENTION

Field of the Invention

The present invention relates to a surgery supporting apparatus for controlling motion of a robot arm, a control method of the same, and a non-transitory computer-readable storage medium.

Description of the Related Art

A laparoscopic surgery is generally performed by a doctor (to be referred to as "an operator" hereinafter) who performs incision, excision, and suture of an organ, a doctor (to be referred to as "a scopist" hereinafter) who holds an endoscope, and a doctor (to be referred to as "an assistant" hereinafter) who performs, for example, organ retraction to increase visibility for the operator, and tension retainment during incision. Some surgery supporting apparatuses (also called surgery supporting robots) for use in a laparoscopic surgery reduce the number of doctors necessary for the surgery by controlling the postures of surgical instruments such as forceps, an endoscope, and an electric scalpel by using one or more robot arms.

The manipulation of a surgery supporting apparatus includes a console type manipulation by which a doctor manipulates a surgery supporting apparatus from a control unit of the apparatus, and a method by which an operator controls, for example, a robot arm for holding only an endoscope while performing a surgical procedure by some method.

Conventional surgery supporting apparatuses to be used in a laparoscopic surgery are roughly classified into an apparatus that performs motions of three doctors, that is, an operator, a scopist, and an assistant, and an apparatus that holds an endoscope with one arm. The apparatus that functions as an operator, a scopist, and an assistant is a console type surgery supporting robot, and robots including a plurality of robot arms arranged around and over a patient are known (Japanese Patent Laid-Open Nos. 2011-4880 and 2017-104455).

On the other hand, a surgery supporting robot that holds only an endoscope by using one robot arm is also known (Japanese Patent Laid-Open No. H6-30896). This surgery supporting robot disclosed in Japanese Patent Laid-Open No. H6-30896 requires no console for manipulations, and uses a method by which an operator or an assistant manipulates the robot by voices.

The console type surgery supporting robot disclosed in Japanese Patent Laid-Open No. 2011-4880 has a large apparatus size, and this sometimes makes it difficult to optimize the positional relationship between a patient and the robot, depending on a balance with another apparatus in an operating room. Also, it is sometimes possible to remotely manipulate the console type robot, but a manipulation console is usually installed in an operating room in which a patient and the robot exist, in order to observe the outer appearance of the patient and communicate with nurses. This is one cause of oppressing the operating room. Even when the apparatus size of the console type surgery supporting robot disclosed in Japanese Patent Laid-Open No. 2017-104455 is decreased, a large complicated console is necessary to manipulate many multijoint robot arms.

The apparatus size of the surgery supporting robot disclosed in Japanese Patent Laid-Open No. H6-30896 can be decreased because a manipulation target is one arm robot. However, the robot still requires works by an assistant and the like, and the robot arm approaches a plurality of humans. This makes it impossible to secure a sufficient robot arm operational area, or the robot arm interferes with an operator or an assistant and influences an operation procedure. Also, when using the voice manipulating means, it is easy to imagine that when manipulating a complicated surgical instrument different from an endoscope, it is difficult to manipulate the surgical instrument as intended.

SUMMARY OF THE INVENTION

The present disclosure has been made in consideration of the aforementioned issues, and realizes a surgery supporting apparatus not requiring a console that is difficult to install in an operating room, and capable of simply manipulating a robot arm.

In order to solve the aforementioned problems, one aspect of the present disclosure provides a surgery supporting apparatus capable of controlling a posture of a first surgical instrument that is inserted into a body cavity and mechanically drivable, by using a second surgical instrument to be inserted into the body cavity, comprising: a robot arm configured to control the posture of the first surgical instrument attached to the robot arm; one or more processors; and a memory storing instructions which, when the instructions are executed by the one or more processors, cause the surgery supporting apparatus to function as: a switching unit configured to switch motion modes for controlling a motion of the robot arm; and a control unit configured to control the motion of the robot arm in accordance with the motion mode, wherein the motion mode includes a first mode in which the second surgical instrument is used to control the first surgical instrument, and a second mode in which the robot arm is moved by a manipulation including contact to the robot arm, and the control unit controls the motion of the robot arm such that the posture of the first surgical instrument is controlled in accordance with the posture of the second surgical instrument, in a case where the motion mode is the first mode, and controls the motion of the robot arm in accordance with the manipulation including contact to the robot arm, in a case where the motion mode is the second mode.

Another aspect of the present disclosure provides, a control method of a surgery supporting apparatus capable of controlling a posture of a first surgical instrument that is inserted into a body cavity and mechanically drivable, by using a second surgical instrument to be inserted into the body cavity, the surgery supporting apparatus including a robot arm configured to control the posture of the first surgical instrument attached to the robot arm, and the control method comprising: switching motion modes for controlling a motion of the robot arm; and controlling the motion of the robot arm in accordance with the motion mode, wherein the motion mode includes a first mode in which the second surgical instrument is used to control the first surgical instrument, and a second mode in which the robot arm is moved by a manipulation including contact to the robot arm, and in the controlling, the motion of the robot arm is controlled such that the posture of the first surgical instrument is controlled in accordance with the posture of the second surgical instrument, in a case where the motion mode is the first mode, and the motion of the robot arm is controlled in accordance with the manipulation including contact to the robot arm, in a case where the motion mode is the second mode.

Still another aspect of the present disclosure provides, a non-transitory computer-readable storage medium storing a program for causing a computer to execute a control method of a surgery supporting apparatus capable of controlling a posture of a first surgical instrument that is inserted into a body cavity and mechanically drivable, by using a second surgical instrument to be inserted into the body cavity, the surgery supporting apparatus including a robot arm configured to control the posture of the first surgical instrument attached to the robot arm, and the control method comprising: switching motion modes for controlling a motion of the robot arm; and controlling the motion of the robot arm in accordance with the motion mode, wherein the motion mode includes a first mode in which the second surgical instrument is used to control the first surgical instrument, and a second mode in which the robot arm is moved by a manipulation including contact to the robot arm, and in the controlling, the motion of the robot arm is controlled such that the posture of the first surgical instrument is controlled in accordance with the posture of the second surgical instrument, in a case where the motion mode is the first mode, and the motion of the robot arm is controlled in accordance with the manipulation including contact to the robot arm, in a case where the motion mode is the second mode.

According to the present invention, it is possible to provide a surgery supporting apparatus not requiring a console that is difficult to install in an operating room, and capable of simply manipulating a robot arm.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 2A is a functional configuration example of a surgery supporting apparatus according to an embodiment;

FIG. 2B is a view schematically showing the way a handheld medical instrument and a robot medical instrument are inserted into a body cavity when using the surgery supporting apparatus according to the embodiment;

FIGS. 14A and 14B are views showing details of the relationship between the first arm of the linear-motion robot arm and the two frames according to the embodiment;

DESCRIPTION OF THE EMBODIMENTS

Exemplary embodiments of the present invention will be explained in detail below with reference to the accompanying drawings. A surgery supporting apparatus according to the present invention includes a robot arm for controlling the posture of a surgical instrument or an end effector inserted into the body cavity of a patient through a sheath tube. The surgery supporting apparatus measures the insertion angle and the insertion depth of a surgical instrument (to be also referred to as a handheld medical instrument hereinafter) to be inserted into the body cavity and actually used in a surgery by an operator. In accordance with the measurement results, the surgery supporting apparatus controls a robot arm 100 for controlling the posture of a surgical instrument or an end effector (both of which will also be referred to as robot medical instruments hereinafter).

(Outline of Robot Arm 100 According to Surgery Supporting Apparatus)

Figure 1B:
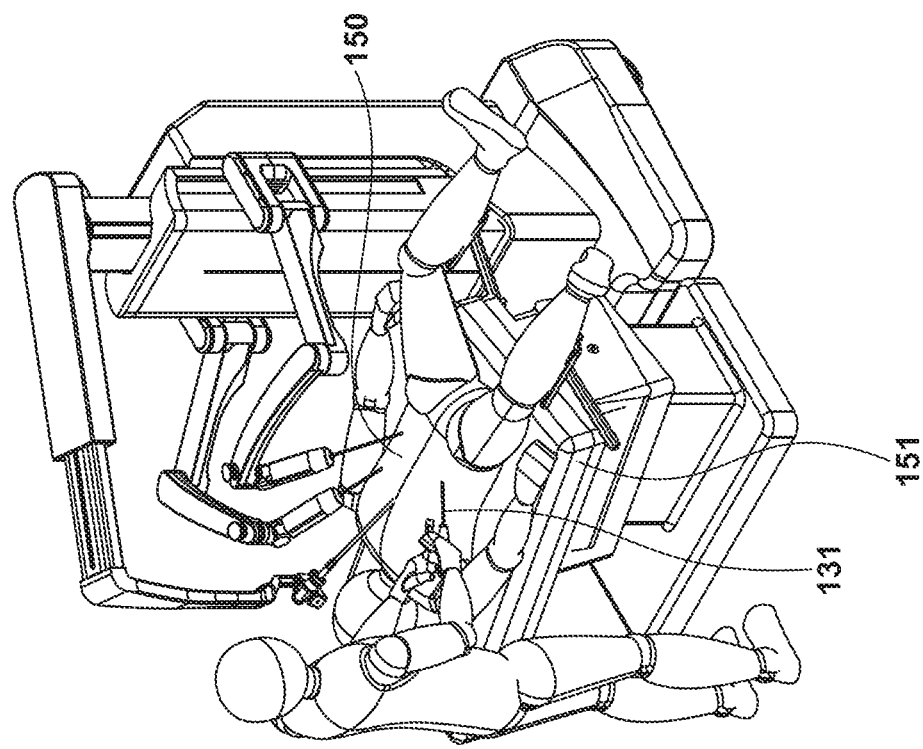
FIGS. 1A and 1B are views showing an overall configuration example of a surgery supporting apparatus according to the present invention.
Figure 1A:
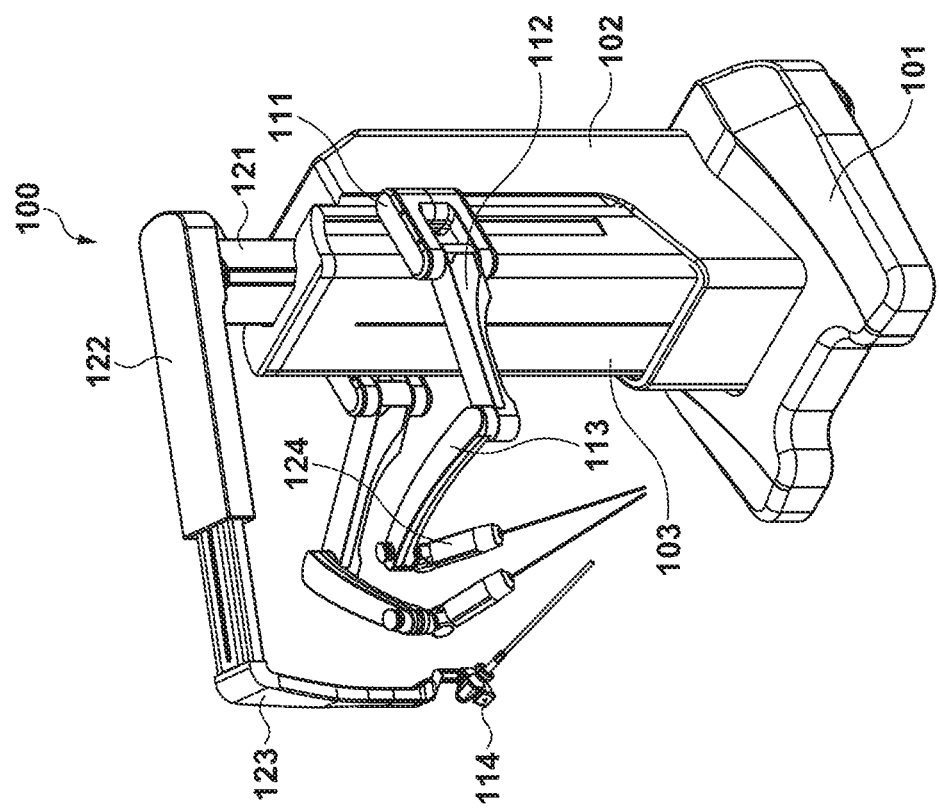

FIG. 1A shows an outline of the robot arm 100 of the surgery supporting apparatus according to the present invention, and FIG. 1B shows a patient, an operator, and an operating table 151 when using a surgery supporting apparatus 200 assumed in this embodiment. The robot arm 100 according to this embodiment includes two horizontal robot arms 110, a linear-motion robot arm 120, and a plurality of frames (bases).

A first frame 101 includes one or both of an active wheel and a passive wheel so as to arrange a patient and the robot arm 100 at an appropriate distance. A second frame 102 is fixed on the first frame 101, and a third frame 103 is connected to the second frame 102 by a part having a degree of freedom in only the vertical direction. Two 3-axis horizontal multijoint robot arms (to be simply referred to as horizontal robot arms 110) including joints having a degree of freedom in the horizontal direction are attached to the third frame 103. In addition, a 3-axis linear-motion multijoint robot arm (to be also simply referred to as a linear-motion robot arm 120) is connected to the distal end of the third frame 103 by a part having a degree of freedom in only the vertical direction.

A surgical instrument manipulator 124 is attached to the distal end of the horizontal robot arm 110 via a gimbal mechanism capable of rotating around two axes. The surgical instrument manipulator 124 is a driving device for controlling the position and posture of the distal end portion of a robot medical instrument whose insertion angle and insertion depth with respect to a body cavity are controlled by the horizontal robot arm 110. The surgical instrument manipulator 124 includes a plurality of motors for generating a plurality of independent rotating powers, and each power is transmitted to the distal end portion of a robot medical instrument through, for example, a shaft of the robot medical instrument.

In the horizontal robot arm 110, a first arm 111 and a second arm 112 are connected by an active joint having a degree of freedom in only horizontal rotation, and the second arm 112 and a third arm 113 are connected by an active joint having a degree of freedom in only horizontal rotation. The first arm 111 includes an active joint having a degree of freedom in the vertical direction (the major-axis direction of the third frame 103), and hence can move the second arm 112 and the third arm 113 in the vertical direction. Since this makes it possible to three-dimensionally move a robot medical instrument connected to the surgical instrument manipulator at the hand of the horizontal robot arm 110, the angle and depth of insertion of the robot medical instrument into a body cavity are controlled. The arrangement of the horizontal robot arm will be described in more detail later.

Like the horizontal robot arm 110, the distal end of the linear-motion robot arm 120 has a gimbal mechanism capable of rotating around two axes. The linear-motion robot arm 120 includes an endoscope holder capable of attaching a general endoscope to the gimbal mechanism. In the linear-motion robot arm 120, a third arm 123 and a second arm 122 are connected by an active joint having a degree of freedom in the horizontal direction, and the second arm 122 and a first arm 121 are connected by an active joint having a degree of freedom in horizontal rotation. Since the first arm 121 is connected to an active joint having a degree of freedom in the vertical direction (the major-axis direction of the third frame 113), the second arm 122 and the third arm 123 can move in the vertical direction. Since this makes it possible to three-dimensionally move an endoscope (robot medical instrument) connected to an endoscope holder 114 at the hand of the linear-motion robot arm 120, the angle and depth of insertion of the endoscope (robot medical instrument) into a body cavity are controlled.

(Arrangement of Surgical Supporting Apparatus 200)

FIG. 2A schematically shows a functional configuration example of the surgery supporting apparatus 200 according to this embodiment, and FIG. 2B schematically shows the way a handheld medical instrument and a robot medical instrument are inserted into a body cavity when using the surgery supporting apparatus 200. The surgery supporting apparatus 200 is not a general console type master-slave apparatus, but controls the motion of a robot arm based on the motion of a surgical instrument (that is, a handheld medical instrument) which an operator uses during a surgery.

A handheld medical instrument 131 is a surgical instrument which an operator actually moves by the hand to perform an ordinary treatment, and is inserted into a body cavity through an operator-side sheath tube 135 inserted into a small-diameter hole formed in an abdominal wall 150. The handheld medical instrument 131 includes, for example, a forceps, a pair of tweezers, an electric scalpel, an aspiration tube, an ultrasonically activated scalpel, a hemostatic device, a radiofrequency ablation device, a medical stapler, and a needle holder to be inserted into a body cavity. A surgical instrument motion measurement unit 132 attached to the handheld medical instrument 131 and an operator-side insertion depth measurement unit 136 attached to the operator-side sheath tube 135 measure the angle and depth of insertion of the handheld medical instrument 131 into the body cavity.

A part of a robot medical instrument 127 is inserted into the body cavity through a robot-side sheath tube 125 inserted into a small-diameter hole formed in the abdominal wall 150. For example, the robot medical instrument 127 includes a forceps, a pair of tweezers, an electric scalpel, an aspiration tube, an ultrasonically activated scalpel, a hemostatic device, a radiofrequency ablation device, a medical stapler, a needle holder, an endoscope, a thoracoscope, and a laparoscope to be inserted into a body cavity. The robot medical instrument 127 can have a straight shape, and can also have a bending joint. In an example of this embodiment, an endoscope as the robot medical instrument 127 is attached to the linear-motion robot arm 120 via the endoscope holder 114. Also, a forceps, an electric scalpel, or the like is attached as the robot medical instrument 127 to the horizontal robot arm 110 via the surgical instrument manipulator 124. The posture of the distal end of the medical instrument such as a forceps attached via the surgical instrument manipulator 124 is controlled by driving the surgical instrument manipulator 124. Note that in this embodiment, a simple term "robot arm" means that the robot arm includes the surgical instrument manipulator 124. Note also that an explanation will be made by taking, as an example, a case in which the robot medical instrument 127 and the surgical instrument manipulator 124 are different members, but the robot medical instrument 127 and the surgical instrument manipulator 124 may also be integrated as a surgical instrument.

A robot-side insertion depth measurement unit 126 can detect that the robot arm is inserted into the robot-side sheath tube 125. Also, one or more distance sensors attached to the robot-side sheath tube 125 measure the depth of insertion, into the body cavity, of the robot medical instrument 127 that is controlled by the horizontal robot arm 110 or the linear-motion robot arm 120. Note that the robot-side insertion depth measurement unit 126 can also detect only the insertion of the robot arm into the robot-side sheath tube 125. In this case, position/posture information can be obtained in accordance with the output from an encoder of the robot arm. Furthermore, the robot-side insertion depth measurement unit 126 can separately be attached to the robot-side sheath tube 125 and the robot medical instrument 127, like a transmitter and a receiver, and can also be attached to only the robot medical instrument 127.

The surgical instrument motion measurement unit 132 includes one or a combination of, for example, an acceleration sensor, an ultrasonic sensor, a geomagnetic sensor, a laser sensor, and an optical motion capture, and detects 3-axis to 6-axis surgical instrument motions. In this embodiment, the surgical instrument motion measurement unit 132 measures, for example, the angle of insertion, into a body cavity, of a handheld medical instrument to be manipulated by an operator.

The operator-side insertion depth measurement unit 136 includes one or more distance sensors attached to the operator-side sheath tube 135, and measures the depth of insertion of the handheld medical instrument 131 into a body cavity. In this embodiment, an example in which the operator-side insertion depth measurement unit 136 is attached to the operator-side sheath tube 135 will be explained. However, the operator-side insertion depth measurement unit 136 can separately be attached to the operator-side sheath tube 135 and the handheld medical instrument 131, like a transmitter and a receiver, and can also be attached to only the handheld medical instrument 131.

A control unit 201 includes one or more processors such as a CPU or a GPU, and controls the overall manipulation of the surgery supporting apparatus 200 by reading out a program stored in a storage medium 204 to a memory 205 and executing the readout program. The control unit 201 also functions as a switching unit (switch) for switching manipulation modes of the surgery supporting apparatus based on a manipulation performed on a manipulation unit 202. Furthermore, the control unit 201 functions as a control unit for controlling the manipulation of a robot arm so as to control the posture of a robot medical instrument in accordance with the insertion angle and the insertion depth of the shaft of the handheld medical instrument 131 with respect to a body cavity. The manipulation modes of the surgery supporting apparatus include a mode (to be also simply referred to as a treatment mode) in which a treatment is actually performed by manipulating the handheld medical instrument 131, and a mode (to be also simply referred to as a robot manipulation mode) in which the robot medical instrument 127 is manipulated by using the handheld medical instrument 131. As will be described in detail later, the manipulation modes also include a mode in which an operator manipulates a robot arm by a manipulation including contact to the robot arm.

The manipulation unit 202 includes manipulation members such as a switch to be attached to the handheld medical instrument 131, and a foot switch which an operator can manipulate with his or her foot. Instead of the switch, the manipulation unit 202 can further include a voice input system by which a manipulation can be input by a voice. In accordance with an input from the manipulation unit 202, the control unit 201 changes the manipulation mode of the surgery supporting apparatus 200, changes an arm to be controlled, and changes information to be displayed on a display unit 203. For example, an operator can select one arm as a control target by using the manipulation unit 202.

As described above, the robot medical instrument 127 can be manipulated in accordance with the motion of the handheld medical instrument 131 manipulated by an operator. Therefore, while three doctors usually perform a conventional laparoscopic surgery, an operator can perform a similar surgery by manipulating the robot arm although the manipulation is equal to that of a surgery performed by manipulating a surgical instrument.

Figure 3:
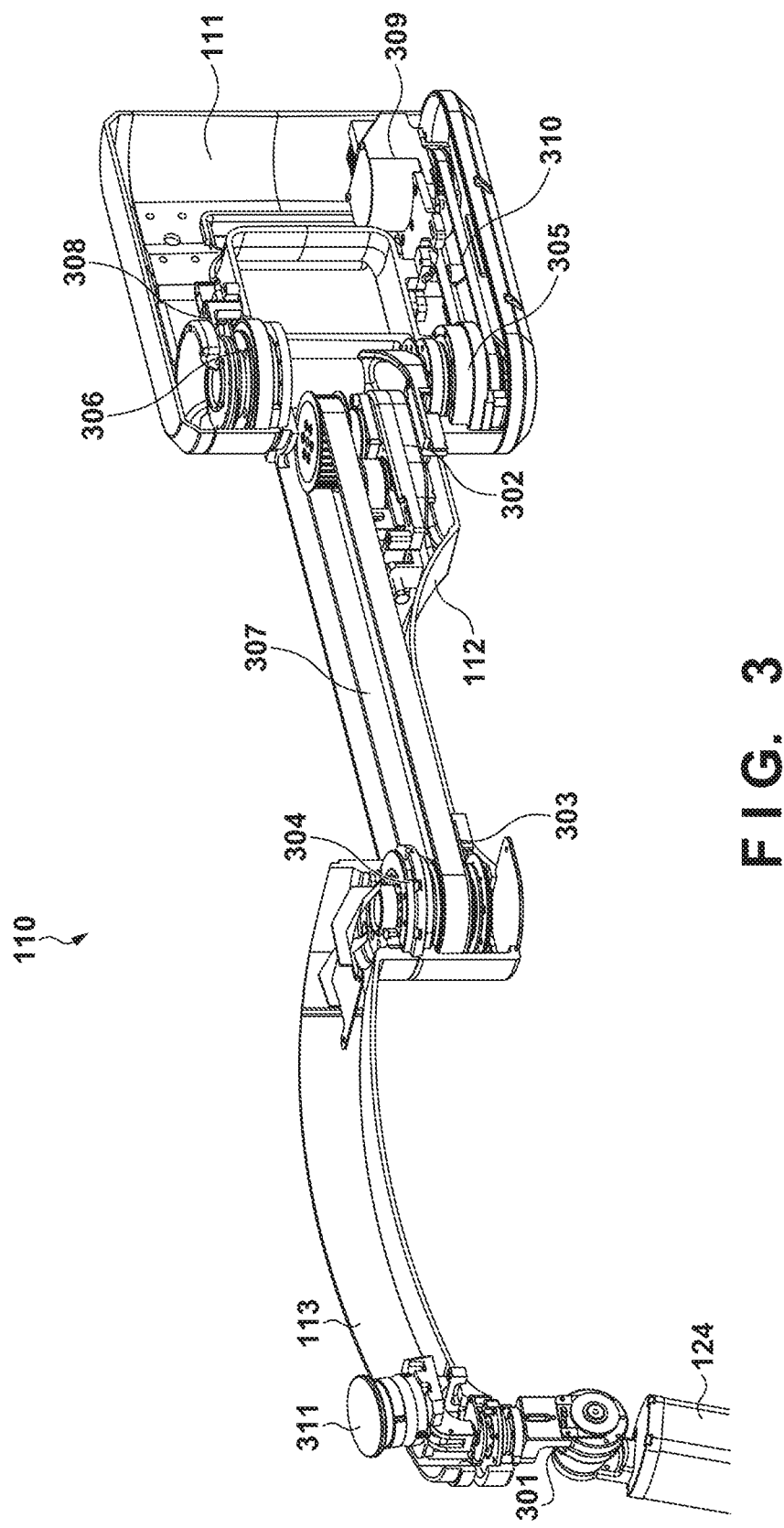
FIG. 3 is a view showing a detailed configuration example of a horizontal robot arm according to the embodiment.
Figure 4:
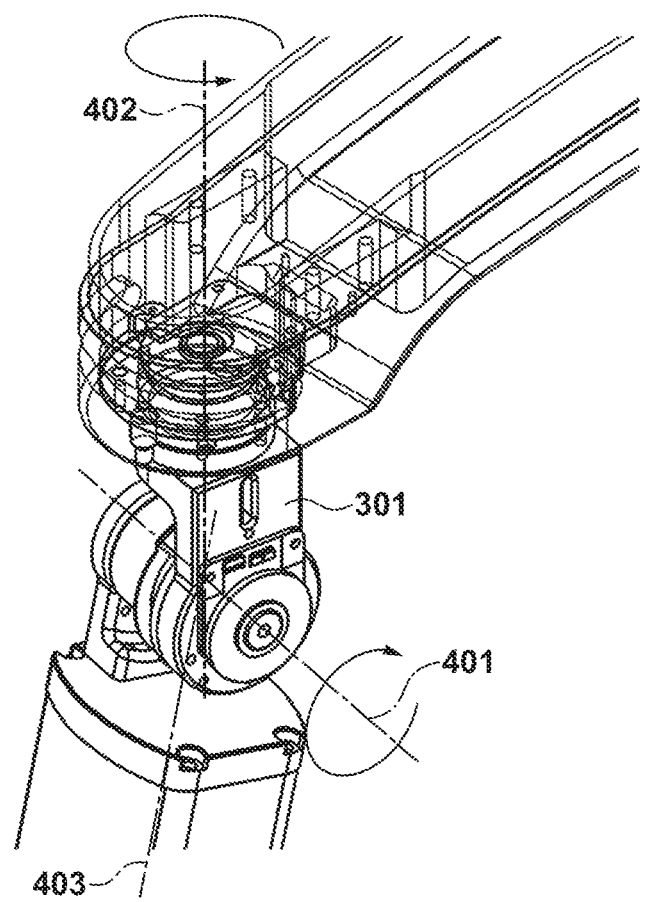
FIG. 4 is an enlarged view of the distal end portion of the horizontal robot arm according to the embodiment.

(Details of Horizontal Robot Arm 110)
<Horizontal Driving Joint>
Details of the horizontal robot arm 110 will be explained with reference to FIGS. 3 to 8. As shown in FIG. 3, the distal end portion (of the third arm 113) of the horizontal robot arm 110 has a 2-axis gimbal mechanism 301 to which the surgical instrument manipulator 124 can be attached. FIG. 4 shows the distal end portion (of the third arm 113) of the horizontal robot arm 110 in an enlarged scale. The gimbal mechanism 301 can rotate around two rotating axes 401 and 402 shown in FIG. 4, and the two rotating axes 401 and 402 intersect an axis 403 of the surgical instrument shaft of a robot medical instrument attached to the surgical instrument manipulator 124. The gimbal mechanism 301 is a passive joint having no power unit, but includes an encoder for measuring rotation around each rotating axis. For example, it is possible, by using absolute encoders for both of the two axes, to obtain the position and posture of the robot medical instrument 127 by using the forward kinematics. Also, the horizontal robot arm 110 can use an elastic mechanism (for example, a damper, a resin spring, or a metal spring in the rotational direction) or an auxiliary power in order to suppress the influence of slight vibrations during manipulation or slight motions caused by the respiration of a patient, thereby achieving a function of stabilizing the posture or avoiding a unique posture.

A third arm driving unit 302 contained in the second arm 112 includes a driving motor for driving the third arm 113, a spring-actuated brake, and a speed reducer. The third arm 113 and the second arm 112 have a degree of freedom in only horizontal rotation, and the third arm 113 can actively rotate by receiving, by using a timing pulley, the power output from the third arm driving unit 302 by a timing belt 307. The second arm 112 has a third arm sensor unit 303 for measuring the rotation of the third arm 113 with respect to the second arm. The third arm sensor unit 303 includes an encoder for detecting the rotational position around the rotating shaft of the joint connecting the third arm 113 and the second arm 112, and other sensors. The rotating shaft of this joint has a bearing 304.

The first arm 111 supports the second arm 112 by the frame having a C-shaped structure. In this frame, a speed reducer 305 including a bearing capable of permitting the moment is arranged on one side, and an auxiliary bearing 306 as an auxiliary member is arranged on the other side. This makes it possible to disperse the moment generated from the weights of the third arm 113, the second arm 112, the surgical instrument manipulator 124, and the robot medical instrument 127, and from the external force. A second arm driving unit 309 contained in the first frame 111 transmits the power for rotating the second arm 112 by a driving belt 310, thereby rotating the second arm 112 around the rotating shaft of the joint (the connecting portion between the third arm 113 and the second arm 112). Also, a large hollow structure is secured by distributing the mechanisms in the first frame 111. This makes it possible to attach wires and an encoder 308 for detecting the rotational position of the second arm 112 with respect to the first arm 111. In this example shown in FIG. 3, the speed reducer 305 incorporating the bearing capable of permitting the moment is arranged in the lower portion of the first frame 111, and the hollow structure is formed in the upper portion. However, these positions may also be switched.

This embodiment is explained by taking, as an example, the case in which the output mechanisms such as the speed reducer 305 and the second arm driving unit 309 are formed into flat shapes in order downsize the horizontal robot arm 110. For example, it is possible to use a harmonic drive gear speed reducer or a cycloidal speed reducer capable of high speed reduction even with a flat shape, a flat motor for which the output of the motor itself is raised, or a direct driver motor that can be attached directly to the joint. As a bearing to be used in the four rotating joints, a cross roller bearing or a 4-point bearing can be used so as to downsize the mechanism while permitting the moment.

<Vertical Driving Joint>

Figure 5:
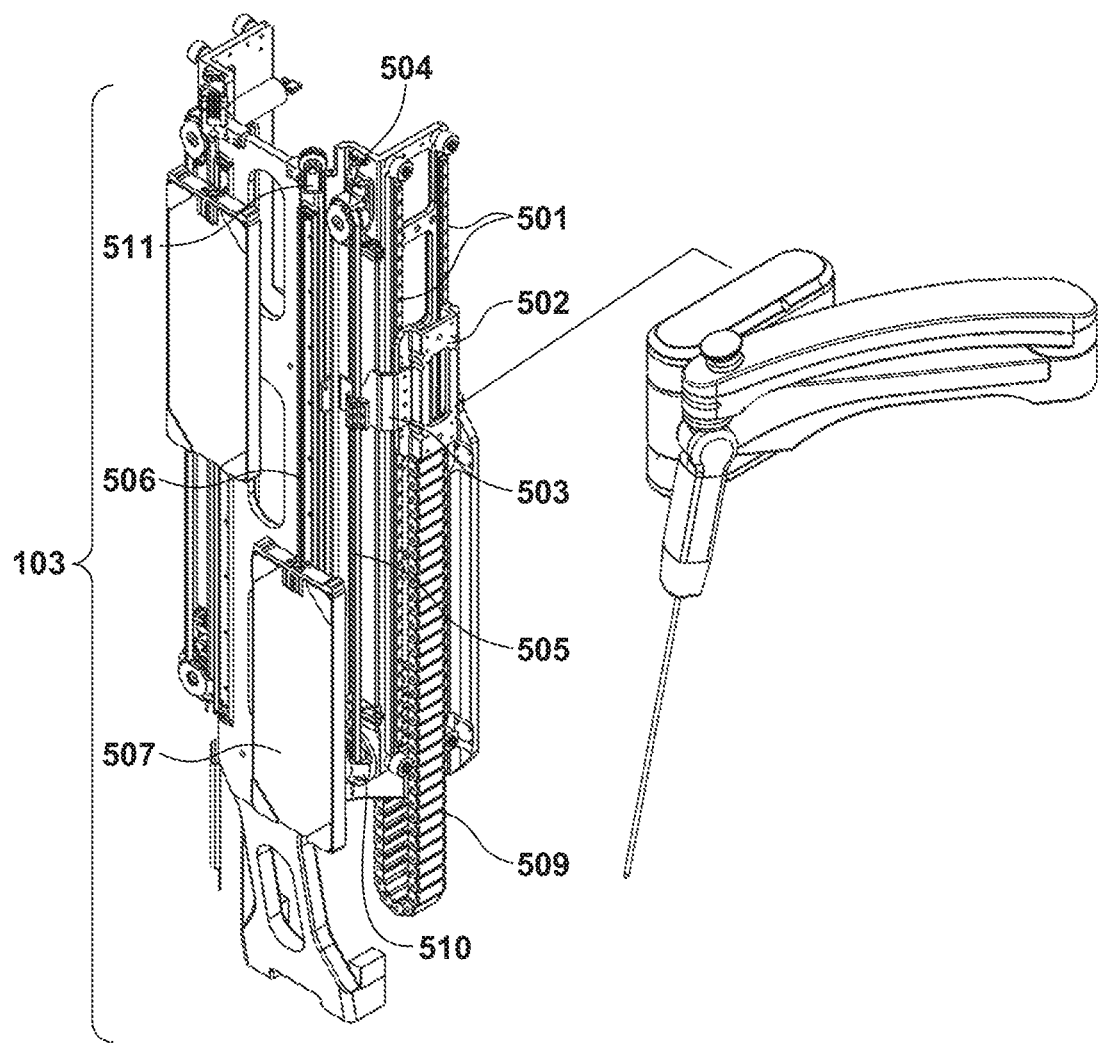
FIG. 5 is a view showing a configuration example of a linear-motion joint of the horizontal robot arm according to the embodiment.

FIG. 5 shows a linear-motion joint of the horizontal robot arm 110. This linear-motion joint is incorporated into the third frame 103. In a linear-motion mechanism for driving the first arm 111, two ball linear guides 501 are arranged in parallel in the vertical direction. The ball linear guides 501 can sufficiently permit the weight moments of the first, second, and third arms 111, 112, and 113 and the external forces which the arms receive, and smoothly move these arms.

The first arm 111 is fixed to a support block 502 attached to the ball linear guides 501. A timing belt 505 is fixed to a power transmitting plate 503 extending from the support block 502 supporting the first arm 111, and arranged parallel to the ball linear guides 501. A driving motor 504 transmits a rotating power to the timing belt 505 and drives the timing belt 505 by a timing pulley, thereby actively moving the support block 502 supporting the first arm forward and backward in the vertical direction. A position detection control unit 510 including an encoder measures the vertical moving amount of the first arm 111 based on the moving amount of the driving belt 505 having moved forward and backward. Also, the position detection control unit 510 includes a braking mechanism, and brakes the motion of the support block 502 (that is, the linear motion of the horizontal robot arm 110) so as to maintain the posture. Note that an example using the braking mechanism will be explained in this embodiment, but the braking mechanism need not always be used. In this case, a state in which the driving motor 504 is generating a driving force for maintaining the posture is maintained. A counterweight 507 is connected to the power transmitting plate 503 by a retraction wire 506 supported by a support pulley 511.

The counterweight 507 can suppress the output of the driving motor 504 for driving the first, second, and third arms 111, 112, and 113, the surgical instrument manipulator 124, and the robot medical instrument 127, by compensating for the weights of these members. The counterweight 507 according to this embodiment will be explained in more detail below. In addition to a manipulation from a handheld medical instrument manipulated by an operator, the horizontal robot arm 110 must manually be moved directly when preparing a surgery or in case of emergency. In a case like this, a horizontal driving joint can easily be moved by human hands by only releasing the brake. When the brake of a vertical driving joint is released, however, a large weight of the horizontal robot arm 110 must be held by human hands. Therefore, the vertical driving joint shown in FIG. 5 includes the counterweight 507 for compensating for the weight of each member. This makes it possible to reduce the output to the driving member, and manually move the robot arm without feeling the weight of the robot arm. Note that the use of the counterweight 507 is not essential, and a constant load spring may also be used.

Note that when manually moving the robot arm, it is possible to use an assisting system that outputs only power equivalent to the weight of the robot arm in the vertical-axis direction by using a program. When the system is down, however, it may be difficult to manually move the robot arm. By contrast, the counterweight 507 is separated from the system by a logic circuit for releasing the brake and shutting off power supply to the motor. Accordingly, the robot arm is manually movable even when a system error occurs.

Between the two ball linear guides 501 arranged parallel to each other, the third frame 113 includes a cable guide 509 that assists a linear motion of wires in order to connect a signal line and a power line to the third arm 113.

Note that the linear motion mechanism shown in FIG. 5 uses a high-efficiency timing belt pulley in order to facilitate manipulations (back drive ability) from the output side. However, it is also possible to use a ball screw having a large lead, or a high-efficiency slide screw.

<Grip With Brake Release Switch>

In addition to the weight compensation mechanism (the counterweight 507) for making a manual movement of the robot arm possible in accordance with the situation, the horizontal robot arm 110 according to this embodiment includes a brake release switch 311 for facilitating a manual manipulation of the robot arm. As shown in FIG. 6, the brake release switch 311 forms a grip with a switch capable of vertically and horizontally moving the robot arm when grasped with one hand. As will be described later, the brake release switch 311 can be pressed in multiple directions so that a manipulator can press the switch with an almost constant posture, even when the robot arm variously changes its posture with respect to the manipulator.

The brake release switch 311 is arranged in the distal end portion of the third arm 113. The brake release switch 311 includes a switch for releasing a holding brake attached to each joint of the horizontal robot arm 110, and a cylindrical grip to be grasped by an operator or the like.

Figure 6B:
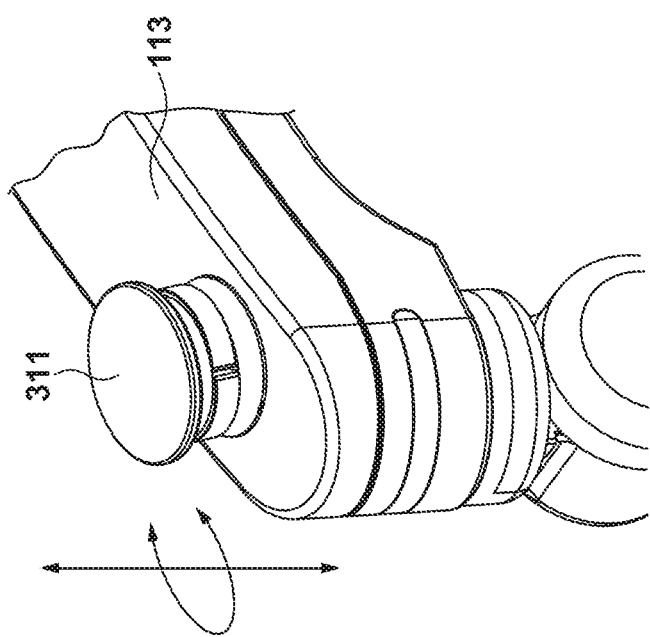
FIGS. 6A and 6B are views for explaining a grip with a brake release switch according to the embodiment.
Figure 6A:
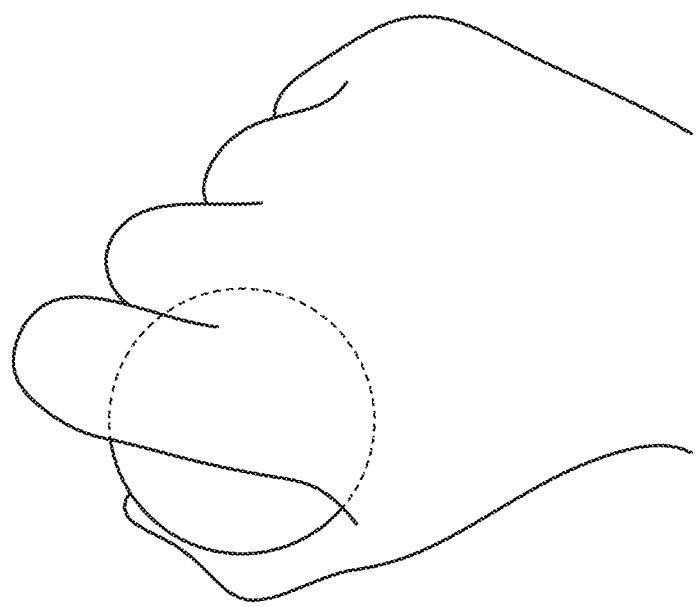

For safety's sake, the brake for maintaining the posture of the robot arm is released only while the brake release switch 311 is pressed. Note that instead of the brake, it is also possible to temporarily decrease the driving force for maintaining the posture. To implement a brake like this, the brake release switch 311 according to this embodiment has a structure by which an operator can stably keep pressing the switch while adding a force for moving the distal end portion of the horizontal robot arm 110. The brake release switch 311 shown in FIG. 6A has a shape that, when an operator grasps the switch with a hand as shown in FIG. 6B, facilitates a horizontal movement of the horizontal robot arm 110, sliding of a horizontal rotation caused by the horizontal movement, and addition of a force in the vertical direction to the horizontal robot arm 110. As shown in FIG. 7, switches are arranged on the circumference of a cylindrical portion of the brake release switch 311, in order to stably press the switch while permitting sliding of a horizontal rotation.

The grip of the brake release switch 311 according to this embodiment is formed into a cylindrical shape, and it is assumed that an operator holds the grip so as to sandwich it between the thumb and the middle finger or the thumb and the index finger. In this case, in order to permit sliding of the rotation of the grip when the horizontal robot arm 110 is horizontally moved, the grip has a mechanism that can react in any direction with contact by which the grip is sandwiched between the two fingers in almost parallel. A manipulator can also grasp the grip so as to cover the whole brake release switch 311 (so that the five fingers come in contact with the cylindrical portion).

Figure 7C:
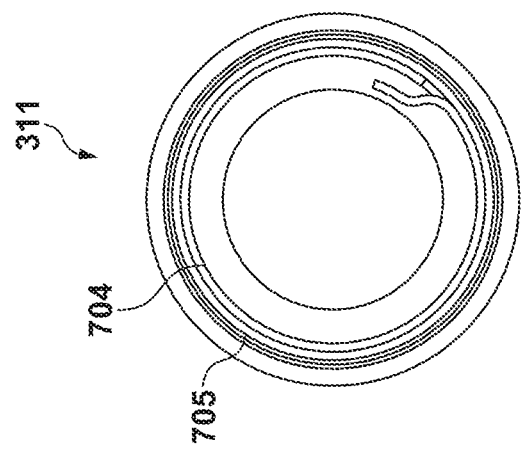
FIGS. 7A to 7C are views showing internal structure examples when the brake release switch according to the embodiment is viewed in the vertical direction.
Figure 7B:
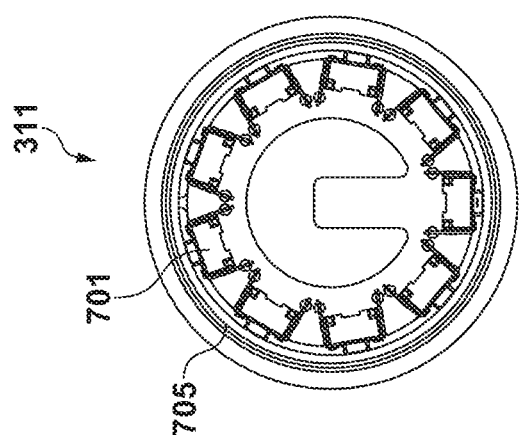
Figure 7A:
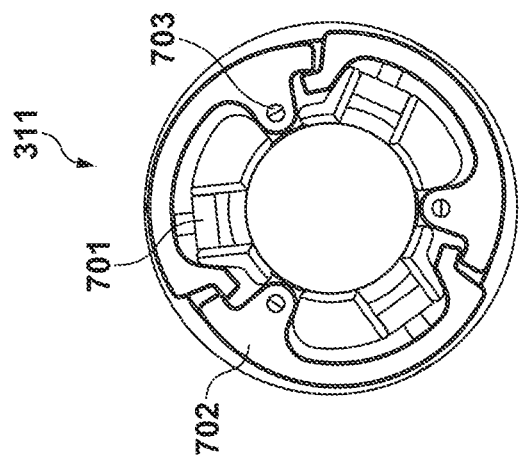

FIGS. 7A to 7C show the internal structures when the brake release switch 311 is viewed in the vertical direction. In an example shown in FIG. 7A, general tact switches 701 are circularly equally arranged, and the outer circumference is surrounded by levers 702 each having a rotation fulcrum 703. In a position farthest from the fulcrum, the pushing amount of the lever 702 is largest, and the force is easily added in the direction of pressing the tact switch 701. However, the force of pressing the tact switch 701 decreases as the position comes closer to the rotation fulcrum. Therefore, an odd number of three or more pairs of the tact switches 701 and the levers 702 are arranged at equal intervals. This makes it possible to press the tact switch 701 by one of the two fingers regardless of the direction in which the grip is held.

Note that the lever 702 need not have the rotation fulcrum and may also be pushed parallel toward the center of the grip. As described above, however, an odd number of three or more levers are desirably arranged.

FIG. 7B shows an example in which an odd number of three or more tact switches 701 are arranged at equal intervals, and the outer circumference is surrounded by an elastic resin 705, so that the tact switch 701 is pressed regardless of the direction in which the grip is held. In this example, the number of the tact switches 701 is larger than that of the example shown in FIG. 7A, in order to obtain a high switch sensitivity. In an example shown in FIG. 7C, a general belt-like pressure-sensitive switch 704 (that changes the resistance value when pressurized) is arranged in a cylinder, and the outer circumference is surrounded by the elastic resin 705. Accordingly, the switch can be pressed regardless of the direction in which the grip is held.

<Vector Manipulation Mode>

The brake release switch 311 shown in FIGS. 6 and 7 facilitates manipulating the robot arm when largely moving the horizontal robot arm 110 or after the robot medical instrument 127 is inserted into the robot-side sheath tube 125. On the other hand, in a state in which the distal end portion of the robot medical instrument 127 is not inserted into the robot-side sheath tube 125, the directions of the surgical instrument manipulator 124 and the robot medical instrument 127 are unstable because the 2-axis gimbal mechanism 301 is a passive joint. This sometimes makes manipulation difficult when inserting the robot medical instrument 127 into the robot-side sheath tube 125.

Figure 8:
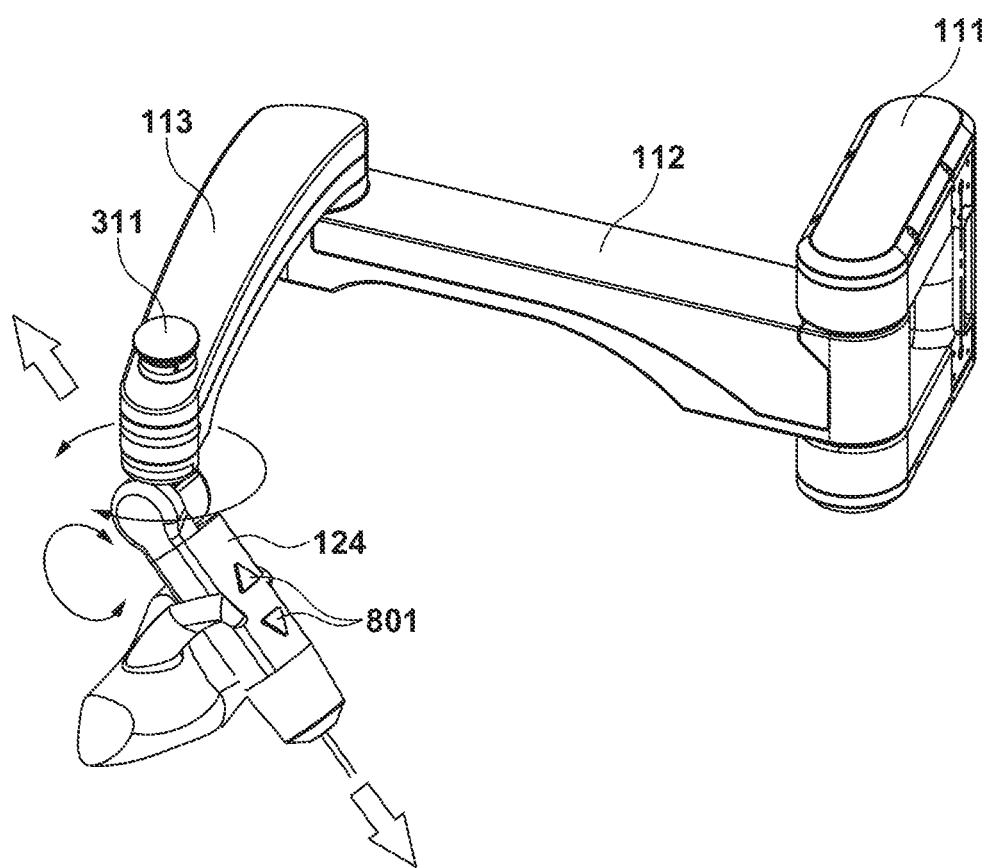
FIG. 8 is a view showing an example of an input switch on the side of a surgical instrument manipulator for a vector manipulation mode according to the embodiment.

In this embodiment, therefore, two input switches are formed on the surgical instrument manipulator 124 as the distal end of the 2-axis gimbal mechanism 301 as shown in FIG. 8, and there is provided a vector manipulation mode in which the whole robot arm can be manipulated based on manipulations on these input switches.

The two input switches represent only the forward and backward directions, and an operator can input an instruction by pressing one of these forward and backward switches while supporting (touching) the distal end of the 2-axis gimbal mechanism 301 with a hand. The horizontal robot arm 110 moves the distal end of the robot arm in a direction matching the pressed direction on the axis of the shaft of the robot medical instrument 127. Since, therefore, the surgical instrument manipulator 124 functions as a manipulating unit for manually manipulating the 2-axis gimbal mechanism 301, the progressing direction of the whole robot arm can be determined. In other words, the horizontal robot arm 110 controls the motion in accordance with the axial direction of the shaft of the robot medical instrument 127, and with the direction indicated by an instruction on the switch with respect to the axial direction of the shaft. This makes it possible to easily and smoothly insert the distal end portion of the robot medical instrument 127 into the robot-side sheath tube 125. Also, when removing the distal end of the robot medical instrument 127 from the body cavity, a removing action that minimizes the contact to an organ can be performed by using this vector manipulation mode.

Note that an example in which the brake release switch 311 and the vector manipulation mode are used in the horizontal robot arm 110 has been explained above, but the same can apply even when using the endoscope holder 114 and the linear-motion robot arm 120.

Figure 9:
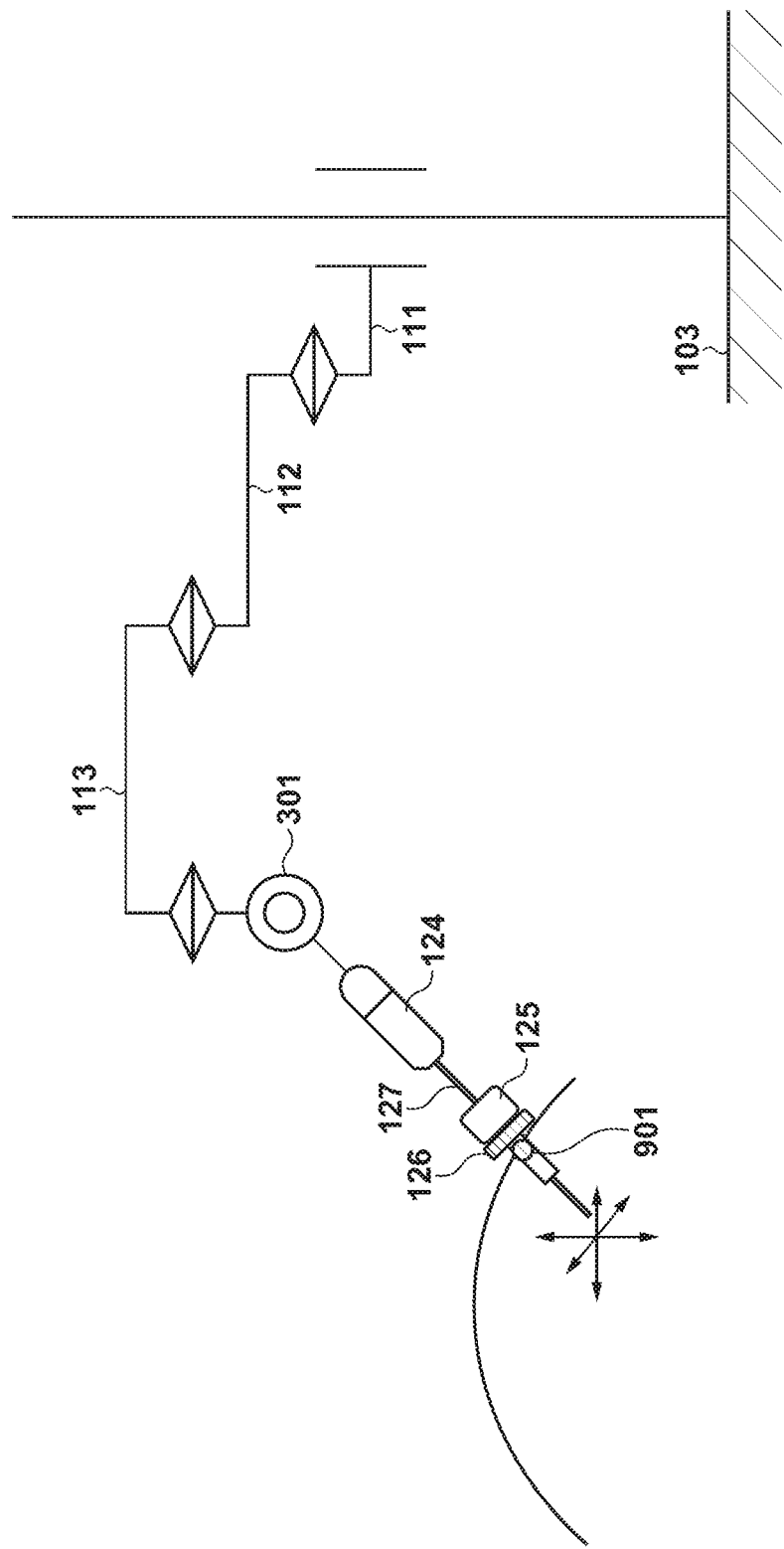
FIG. 9 is a view showing a mechanism equivalent model of the horizontal robot arm according to the embodiment.

The mechanism described above with reference to FIGS. 3 to 5 becomes a 5-axis mechanism equivalent model shown in FIG. 9 by connecting the surgical instrument manipulator 124 and the robot medical instrument 127 to the mechanism. The degrees of freedom of two axes are fixed by inserting the distal end portion of the robot medical instrument 127 having the degrees of freedom of five axes into a sheath tube attached to the abdominal region of a patient. Accordingly, it is possible to three-dimensionally control the position of the distal end portion of the robot medical instrument 127 in the body cavity of the patient, while using an insertion point 901 as the reference point of the insertion depth and the insertion angle.

(Details of Linear-Motion Robot Arm)

<Linear Driving Joint>

Figure 10:
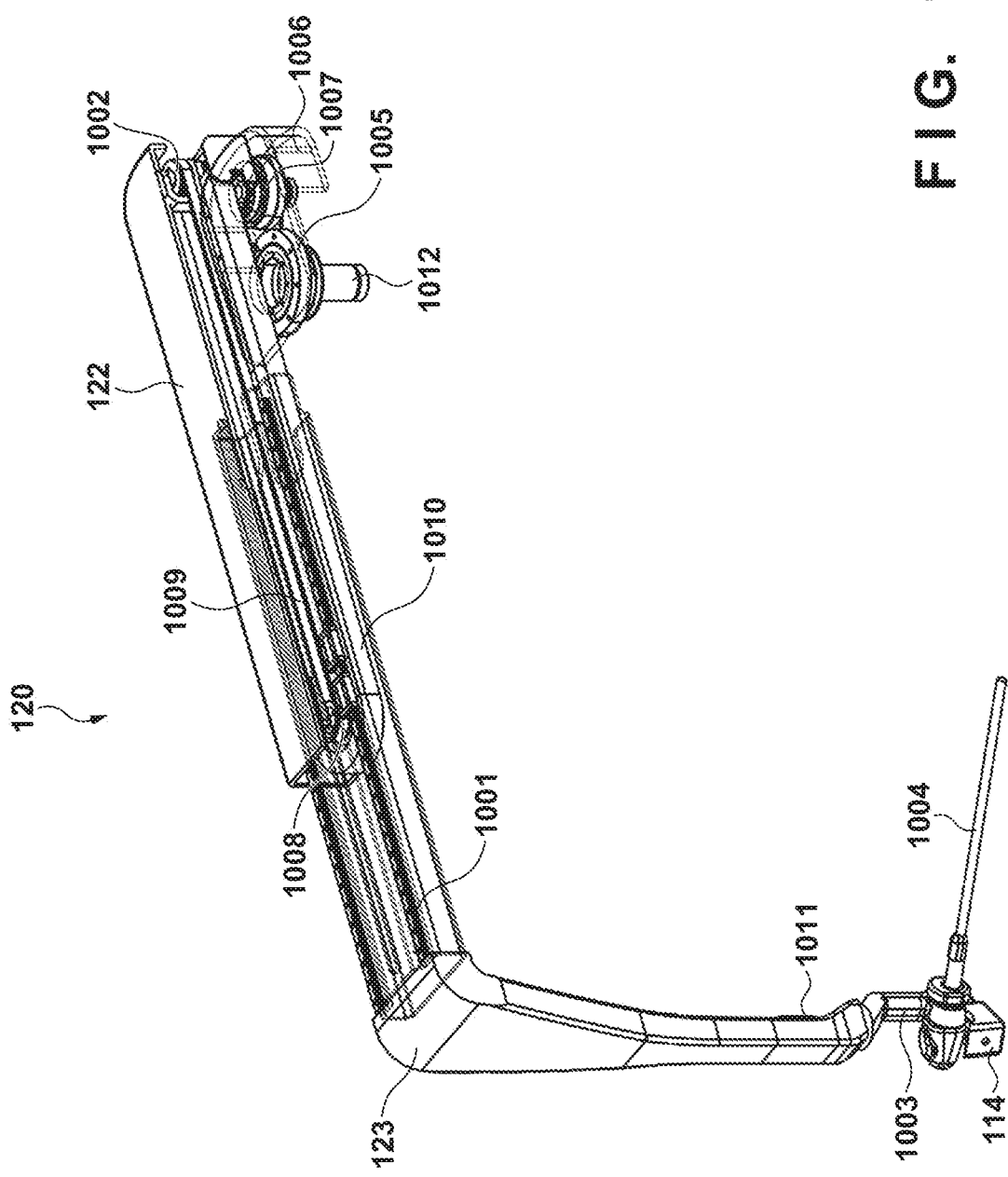
FIG. 10 is a view showing a detailed configuration example of a linear-motion robot arm according to the embodiment.

Details of the linear-motion robot arm 120 will be explained with reference to FIGS. 10 to 12. As shown in FIG. 10, the third arm 123 and the second arm 122 are connected by two ball linear guides 1001 arranged parallel in the horizontal direction, in order to sufficiently permit the weight moment and the external force which the linear-motion robot arm 120 receives, and implement a smooth motion.

A driving unit 1002 fixed to the second arm 122 and including a speed reducer and a motor drives the third arm 123. The other end is fixed to the end of the third arm 123, so the driving unit 1002 can linearly move in the horizontal direction. A third arm sensor unit 1008 measures the forward/backward motion of the third arm 123 based on a change in third arm driving belt 1009 driven by the driving unit 1002. This timing belt pulley and a cable guide for assisting the linear motion of wires are incorporated into the second arm 122 and the third arm 123. A cable guide 1010 that assists the linear motion of wires in order to connect a signal line and a power line to the third arm 123 is installed between the two ball linear guides 1001 arranged parallel to each other.

Like the horizontal robot arm 110, a 2-axis gimbal mechanism 1003 having an encoder is attached to the distal end of the third arm 123, and the endoscope holder 114 can be attached on the axis of the 2-axis gimbal mechanism 1003. A generally used endoscope 1004 can be attached to the endoscope holder 114. Endoscopes manufactured by various manufacturers and having various functions and shapes can be attached to the surgery supporting apparatus by using the endoscope holder 114 matching the endoscope shape as needed. Also, a brake release switch 1011 is arranged near the distal end of the third arm 123.

A first arm connecting plate 1006 attached via a connection bearing 1005 capable of permitting the moment includes a speed reducer 1007. A horizontal rotation can be performed around the rotating axis in the vertical direction by transmitting the power of a second arm driving motor 1012 by a timing belt pulley. Note that it is also possible to directly attach a speed reducer having a hollow structure capable of permitting the moment to the connecting portion between the first arm 121 and the second arm 122 without using the first connecting plate 1006.

The 2-axis gimbal mechanism 1003 at the distal end portion of the third arm 123 is a passive joint having no power unit, like the horizontal robot arm 110. However, it is possible, by using absolute encoders for both of the two axes, to obtain the position of the robot medical instrument 127 by using the forward kinematics. It is also possible to use an elastic mechanism (a damper, a resin spring, or a metal spring in the rotating direction) or an auxiliary power in order to suppress the influence of slight vibrations during robot arm manipulation or slight motions caused by the respiration of a patient, thereby achieving a function of stabilizing the posture or avoiding a unique posture.

<Vertical Driving Joint>

The vertical driving joint of the linear-motion robot arm 120 will be explained below with reference to FIG. 11. The first arm 121 is driven by a nut rotation type ball screw. Therefore, a ball screw shaft 1101 is fixed to the second frame 102, and the lower portion of the first arm 121 as the driving side has a driving unit 1102 including a nut for making rotation possible, a motor for driving the nut, a speed reducer, and an encoder. A generally used mechanical part can be used as this nut rotation type ball screw.

Like the horizontal robot arm 110, the first arm 121 includes a counterweight 1103 that is connected by a wire and compensates for the weight. This makes it possible to suppress the output of the motor in the driving unit 1102, and easily move the robot arm by a direct-contact manual manipulation. Two or more counterweights 1103 are divisionally arranged in the second frame 102 via a support pulley 1106 or the like. This effectively downsizes the whole apparatus while increasing the safety of the wire. A cable guide 1105 assists the motion of a cable or the like extending from the second frame 102 to the first arm 121. Note that the use of the counterweight 1103 is not essential, and a constant load spring may also be used.

The first arm 121 is connected to the second arm 122 via a connecting portion 1104. The second arm 122 is so connected as to be rotatable around the vertical axis of the connecting portion 1104.

Figure 11:
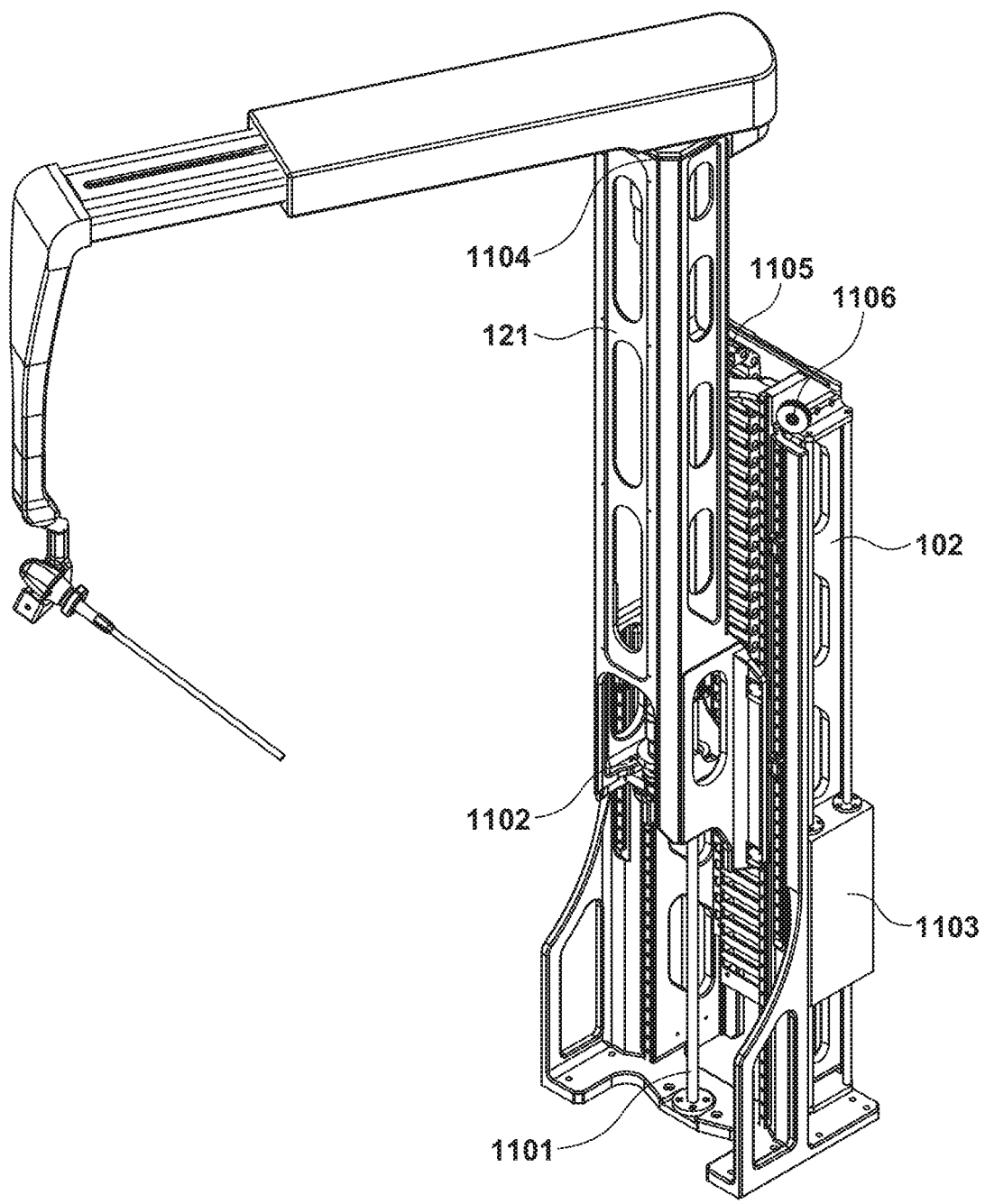
FIG. 11 is a view showing a configuration example of a vertical driving joint of the linear-motion robot arm according to the embodiment.
Figure 12:
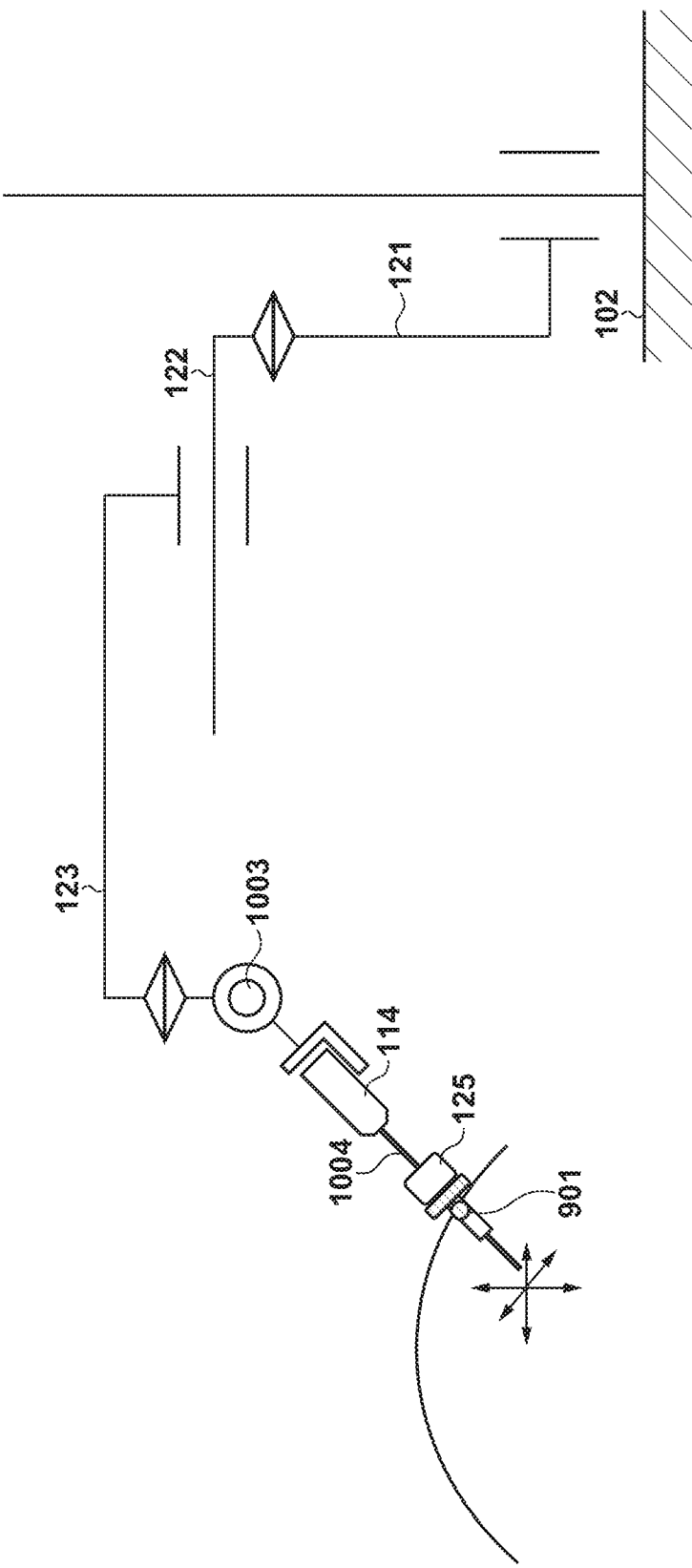
FIG. 12 is a view showing a mechanism equivalent model of the linear-motion robot arm according to the embodiment.

A 5-axis mechanism equivalent model as shown in FIG. 12 is obtained by connecting, via the endoscope holder 114, an endoscope 1004 to the mechanism of the linear-motion robot arm 120 shown in FIGS. 10 and 11. The distal end portion of this endoscope having the degrees of freedom of five axes is inserted into the robot-side sheath tube 125 attached to the abdominal region of a patient. Consequently, it is possible to fix the degrees of freedom of two axes, and three-dimensionally control the position of the distal end portion of the endoscope in the body cavity while using the insertion point as the rotation center.

(Sharing of Screw Shaft)

A laparoscopic surgery is applied to various diseases, and its surgical methods are also various. The operating table 151 shown in FIG. 1B can be moved in the vertical direction by about a maximum of 500 mm in accordance with the surgical method, the body shape of a patient, the height of an operator, and the like. The surgery supporting apparatus according to this embodiment can secure a motion amount corresponding to the height of the operating table that changes in accordance with a change in situation.

Figure 13:
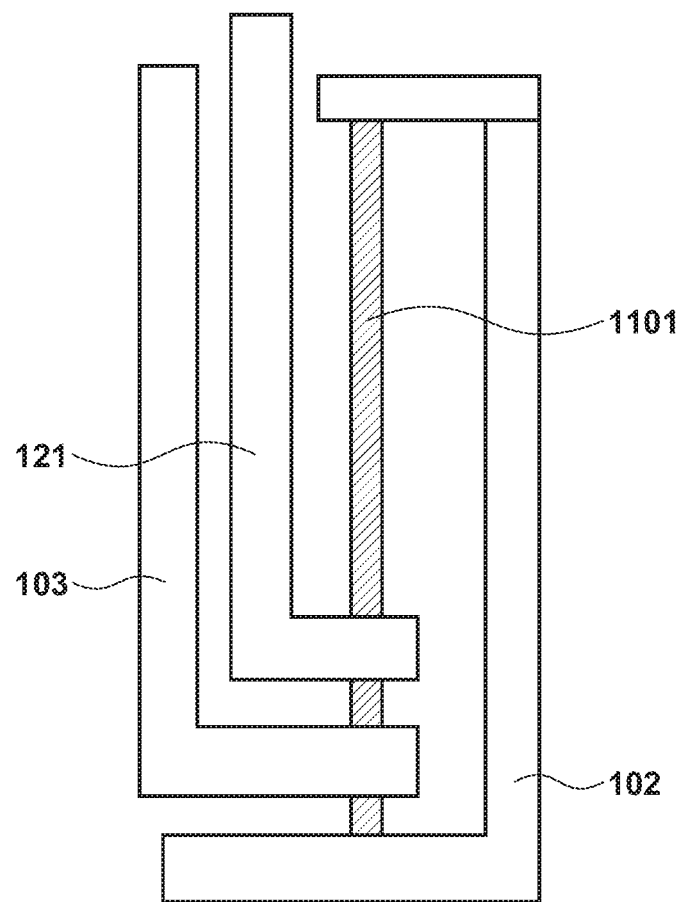
FIG. 13 is a view schematically showing the relationship between the first arm of the linear-motion robot arm and two frames according to the embodiment.

Generally, the height of the whole apparatus increases in order to secure a wide motion amount. However, the height of the operating table does not always change during a surgery, but is determined at the start of a surgery by factors such as the surgical method mentioned above, and does not often change during the surgery. In this embodiment to be explained below, therefore, a motion range that is always movable during a surgery and a motion range that is changed in accordance with the height of the operating table are mechanically separated and at the same time shared as well. This makes it possible to secure a sufficient motion range while reducing the apparatus size. More specifically, FIG. 13 schematically shows the relationship between the first arm 121 of the linear-motion robot arm 120 and the two frames (the second frame 102 and the third frame 103) according to this embodiment. FIG. 14A shows the way the horizontal robot arm 110 is attached to the third frame.

For example, to cause the vertical driving joint of the horizontal robot arm 110 to have a motion range including both the change in height of the operating table 151 and the motion range of the surgical instrument manipulator, a high frame is necessary, and the height of the linear-motion robot arm 120 increases accordingly. When the height of the operating table has changed, therefore, the height is adjusted by vertically moving the third frame 103. When controlling the motion of the handheld medical instrument 131, two steps of strokes can be ensured by individually vertically moving the two horizontal robot arms 110 (that is, the first arms 111) connected to the third frame 103. As shown in FIGS. 13 and 14A, not only the height but also the whole apparatus size can be decreased by attaching the third frame 103 and the first arm 121 of the linear-motion robot arm 120 to a common support member so that these members can move forward and backward.

FIG. 14B is a sectional view showing the frames according to this embodiment. The third frame 103 and the first arm 121 of the linear-motion robot arm 120 have U-shapes so that they can be overlapped while maintaining a high rigidity with respect to the moment in a falling direction. Furthermore, the apparatus can be downsized by sharing parts by arranging the ball screw shaft 1101 in the center of the apparatus.

Generally, many ball screws are linearly moved by attaching a bearing to the end of the shaft, fixing a nut to the driving side, and rotating the screw shaft. On the other hand, this embodiment uses a nut rotation type ball screw to make two linear motions (that is, the linear motions of the third frame and the first arm 121) possible by using one screw shaft 1101. Since the screw shaft is shared, when the third frame 103 rises, the first arm 121 of the linear-motion robot arm 120 rises accordingly, so the lower-limiting motion range of the first arm 121 narrows. However, practically no problem arises because the first arm of the linear-motion robot arm 120 does not require the lower-limiting motion range any longer in accordance with the height of the operating table 151. That is, since one screw shaft 1101 is shared in the linear motions of the third frame and the first arm 121, it is possible to downsize the apparatus and decrease the cost without any practical inconvenience such as a restriction on the robot arm movable range required for a surgery.

(Motion Range of Each Robot Arm)

Figure 15A:
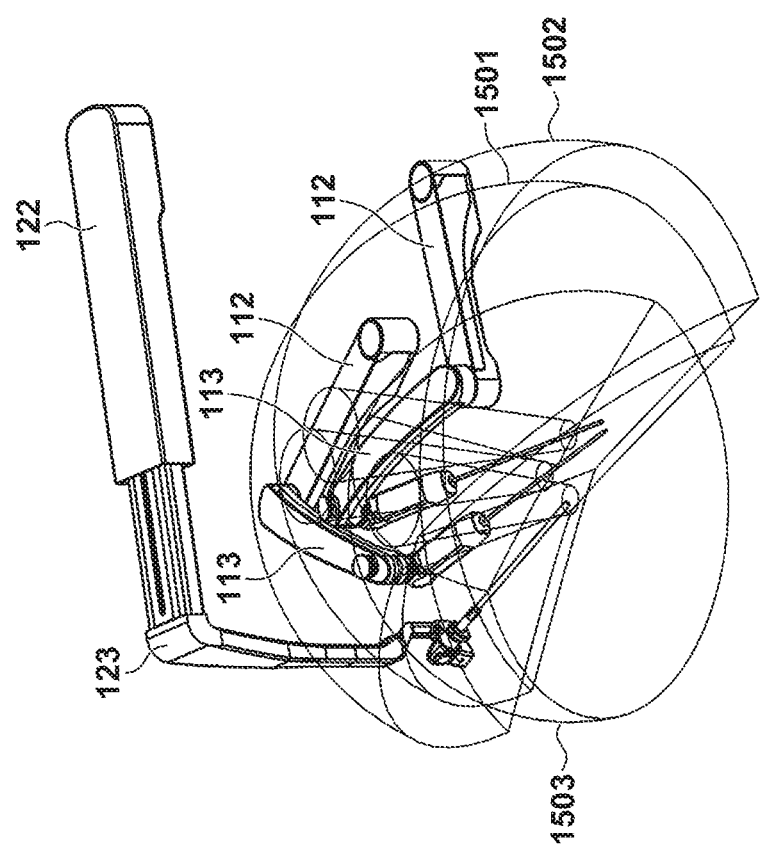
FIGS. 15A and 15B are views each for explaining the movable range of the arm distal end portion of a robot arm according to the embodiment.
Figure 15B:
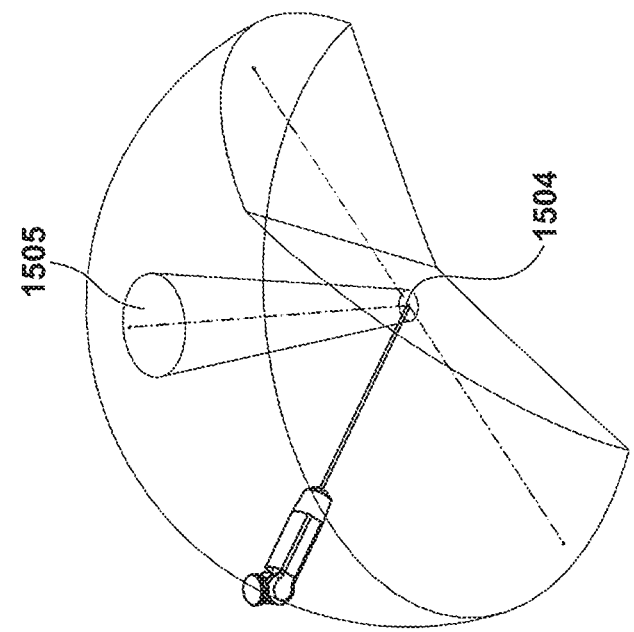

Partial spherical ranges 1501 to 1503 shown in FIGS. 15A and 15B represent examples of the movable range of the arm distal end portion of each robot arm when inserting the robot medical instrument 127 into a body cavity. The center of this spherical range is a position where a sheath tube is inserted into the abdominal region of a patient. A locus corresponding to the surface of the spherical range expresses the arm distal end portion in a position where the distal end portion of the robot medical instrument 127 is extracted most from the robot-side sheath tube 125. Although the movable range of a robot arm alone differs from this, if the arm distal end is moved away from the sheath tube insertion position by a distance longer than the length of the shaft of the robot medical instrument 127, the surgical instrument distal end portion is pulled out from the sheath tube. Accordingly, each spherical range shown in FIGS. 15A and 15B indicate a maximum movable range of the arm distal end portion when inserting the robot medical instrument 127.

A space 1505 immediately above an insertion point 1504 of the robot medical instrument 127 with respect to the sheath tube is a unique posture of the 2-axis gimbal mechanism 301 and hence is excluded from the movable range. The linear-motion robot arm 120 supporting the endoscope 1004 has a similar movable range (for example, 1503), but has a symmetrical spherical motion range in order to minimize interference with the movable range of the horizontal robot arm 110. In an actual surgical method, the robot arm does not always move in this motion range but intensively moves in the lower abdomen or the upper abdomen. Therefore, the range of a shape about half the spherical range is presumably a constant motion range. As shown in FIG. 15A, the movable ranges of the arm distal end portions largely overlap each other, so the horizontal robot arm 110 having a symmetrical structure with respect to the vertical plane is suitable. The vertical robot arm 120 is suitable for an arm capable of supporting the endoscope 1004 so as to avoid these movable ranges.

As is apparent from FIG. 1B described earlier, the arrangement that suppresses the interference of each robot arm from the movable range of the distal end portion of the robot arm when inserting a surgical instrument can avoid interference to the skill of an operator who performs a treatment by using the handheld medical instrument 131 or manipulates the robot arm supporting the robot medical instrument 127, and at the same time can secure a sufficient motion range. Note that the linear-motion robot arm 120 supporting the endoscope 1004 has a similar movable range (1503), and the movable range sometimes contains the hand of an operator. Since, however, the endoscope moves so as to shift the distal end of the handheld medical instrument 131, the direction of the endoscope matches the direction of the handheld medical instrument 131. That is, the interference between the direction of the endoscope and the handheld medical instrument 131 can be suppressed.

Note that each movable range shown in FIG. 15 is an example, so the movable range need not strictly be this range and can be reduced, enlarged, or deformed within the mechanical motion limiting range of the robot arm in accordance with a surgical method or the like.

(Fault Detection System for Robot Arm Having Active Joint)

The surgery supporting apparatus 200 described above can further include a fault detection system for the active joint of each robot arm. To implement this fault detection system, a servo motor having an incremental encoder is used as all motors for driving each robot arm. Also, a spring-actuated brake is installed on the input side or the output side of a speed reducer, and an absolute encoder is installed on the output side.

When a motion instruction is given to the robot arm in an arrangement like this, it is only necessary to determine whether a difference is detected between the command value of the motor and the motion amount on the output side. If it is determined that the difference is detected, it is possible to detect a power transmission abnormality between the motor and the speed reducer, a damage of the speed reducer, and a power transmission abnormality from the speed reducer to the final output shaft. Note that power transmission herein mentioned includes, for example, a gear, a timing belt pulley, a ball screw, and a wire.

On the other hand, even in a standby state in which no motion instruction is given to the robot arm, a difference can be detected between the output-side encoder and the motor encoder when applying the external force to the robot arm. When the external force is given, therefore, whether a difference is detected between the output-side encoder and the motor encoder is determined. If it is determined that the difference is detected, an abnormality such as the external contact of the robot arm is detected.

(Initialization Process)

Figure 16:
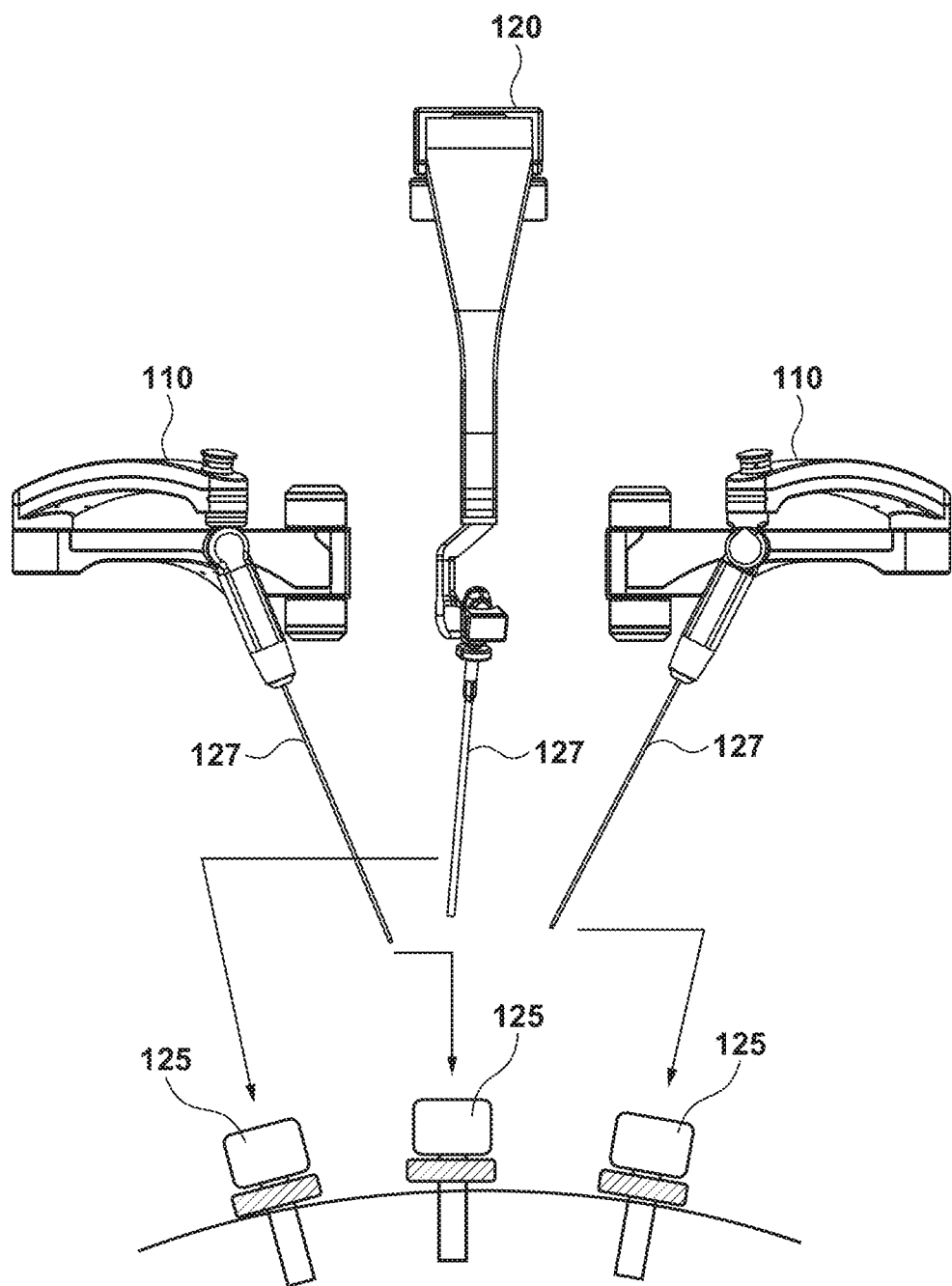
FIG. 16 is a view for explaining initialization according to the embodiment.

Each robot arm of this embodiment has a passive joint. As described above with reference to FIGS. 9 and 12, therefore, when a surgical instrument is inserted into a sheath tube attached to the abdominal region of a patient and the insertion point 901 is determined, the control unit 201, for example, can calculate and specify the position of the distal end of the robot medical instrument 127 in the body cavity. For example, as shown in FIG. 16, an initialization process is performed on each robot arm following a predetermined procedure. This makes it possible to allocate an inserted sheath tube, and obtain position information of the insertion point 901 necessary to control the robot arm.

Figure 17:
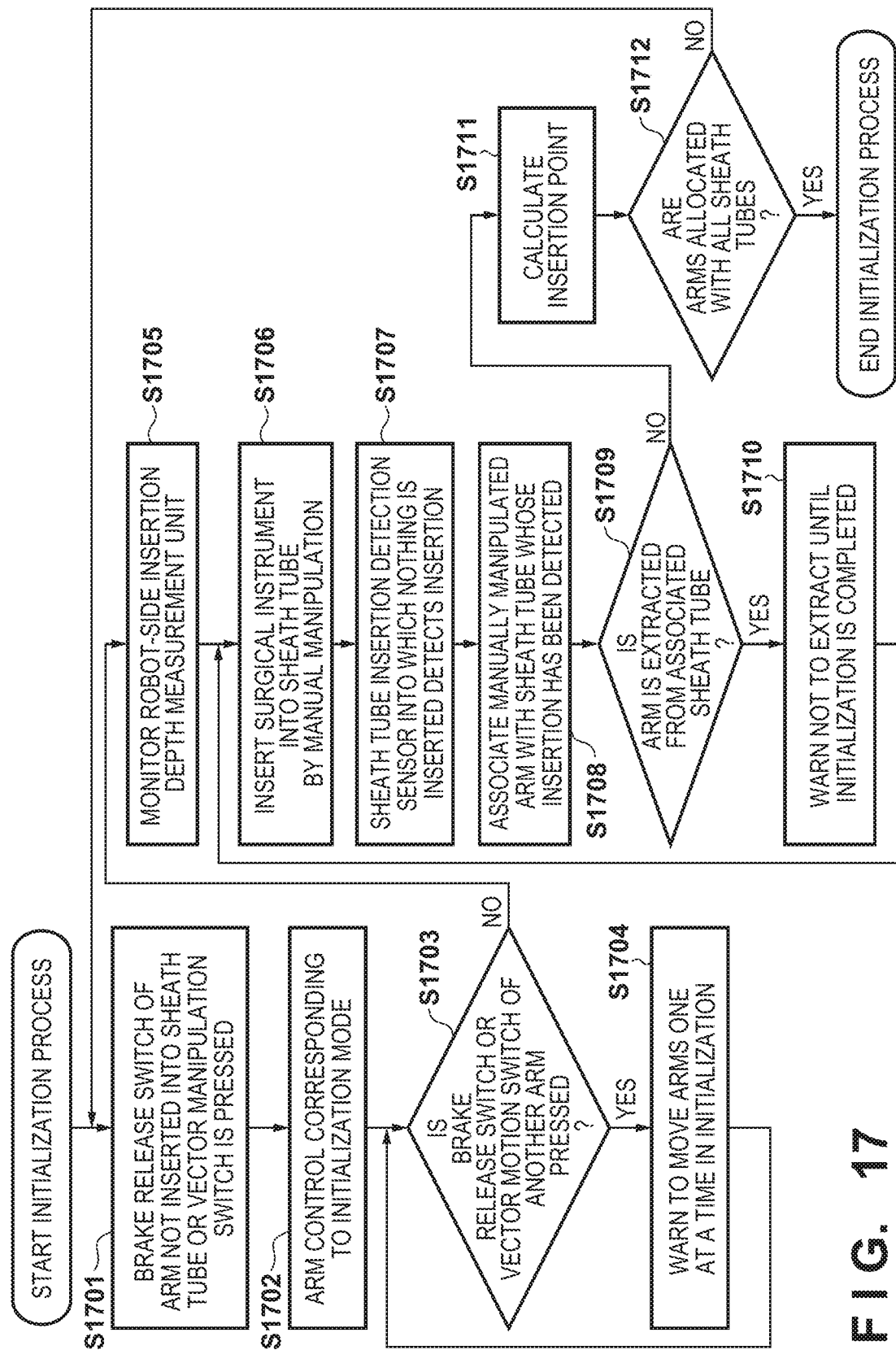
FIG. 17 is a flowchart showing a series of operations of an initialization process according to the embodiment.

A series of operations of the initialization process will be explained with reference to FIG. 17. Note that the control unit 201 executes the operations of an initialization mode shown in FIG. 17 by mapping a program stored in the storage medium 204 to the memory 205 and executing the program. This initialization process is started in a state in which, for example, the operation mode of the surgery supporting apparatus is set to the initialization mode beforehand by a manipulation performed on the manipulation unit 202 (for example, a foot switch) by an operator.

In step S1701, the control unit 201 detects an instruction (for example, switch pressing) by contact of the operator on the brake release switch 311 of the first robot arm not inserted into the robot-side sheath tube 125, or on the vector manipulation switch 801.

In step S1702, the control unit 201 performs robot arm control corresponding to the initialization mode. In accordance with the pressed switch, the control unit 201 can also switch to one of the brake release mode and the vector manipulation mode included in the initialization mode. For example, when the brake release switch 311 is pressed, the control unit 201 sets the operation mode to the brake release mode, and controls the target robot arm so as to release the brake of the robot arm. When the vector manipulation switch 801 is pressed, the control unit 201 switches the operation mode to the vector manipulation mode, and controls the robot arm in accordance with the instruction on the vector manipulation switch 801.

In step S1703, the control unit 201 determines, in an initialization mode for a specific robot arm, whether the brake release switch 311 or the vector manipulation switch 801 of another robot arm is pressed. The control unit 201 advances to step S1704 if it is determined that the brake release switch 311 or the vector manipulation switch 801 of another robot arm is pressed, and advances to step S1705 if not.

In step S1704, in the initialization mode, the control unit 201 causes the display unit 203 to display a warning message indicating an instruction to move robot arms one at a time. This warning is not limited to the display on the display unit 203, and it is also possible to generate a warning sound from a voice output unit (not shown), or give tactile feedback to another manipulated robot arm.

In step S1705, the control unit 201 monitors insertion of the robot medical instrument 127 into the robot-side sheath tube 125, based on the output from the robot-side insertion depth measurement unit 126.

In step S1706, the control unit 201 controls the motion of the robot arm in accordance with a manual manipulation (a manipulation on the grip including the brake release switch 311 or a manipulation on the vector manipulation switch 801) performed by an operator, thereby inserting the robot medical instrument 127 into the robot-side sheath tube 125.

In step S1707, the control unit 201 detects from the robot-side insertion depth measurement unit 126 that the robot medical instrument 127 is inserted into the robot-side sheath tube 125 into which nothing is inserted. In step S1708, the control unit 201 associates the manually manipulated robot arm with the robot-side sheath tube 125 whose insertion has been detected.

In step S1709, based on a signal from the associated robot-side sheath tube 125, the control unit 201 determines whether the robot arm is extracted from the robot-side sheath tube 125. The process advances to step S1710 if it is determined that the robot arm is extracted, and advances to step S1711 if not. In step S1710, the control unit 201 causes the display unit 203 to display a warning message indicating an instruction not to extract the robot arm until the initialization process is complete.

In step S1711, the control unit 201 calculates the position of the insertion point 901. This calculation of the position of the insertion point will be described later. In step S1712, the control unit 201 determines whether the robot arms are associated with all the robot-side sheath tubes 125. If it is determined that the robot arms are not associated with all the robot-side sheath tubes 125, the process returns to step S1701. On the other hand, if it is determined that the robot arms are associated with all the robot-side sheath tubes 125, the control unit 201 switches the operation mode of the surgery supporting apparatus to the original operation mode, and terminates the initialization process.

Two methods will be explained below as examples of the method of calculating the insertion point 901 in step S1711 of the initialization process. In one method, the position of the robot medical instrument 127 detected by a robot-side insertion depth measurement unit that also operates as an insertion detection sensor is regarded as an insertion point. In this method, the control unit 201 can calculate the position of the insertion point in a robot coordinate system by using the forward kinematics from each link length, each surgical instrument length, and each joint angle.

Figure 18:
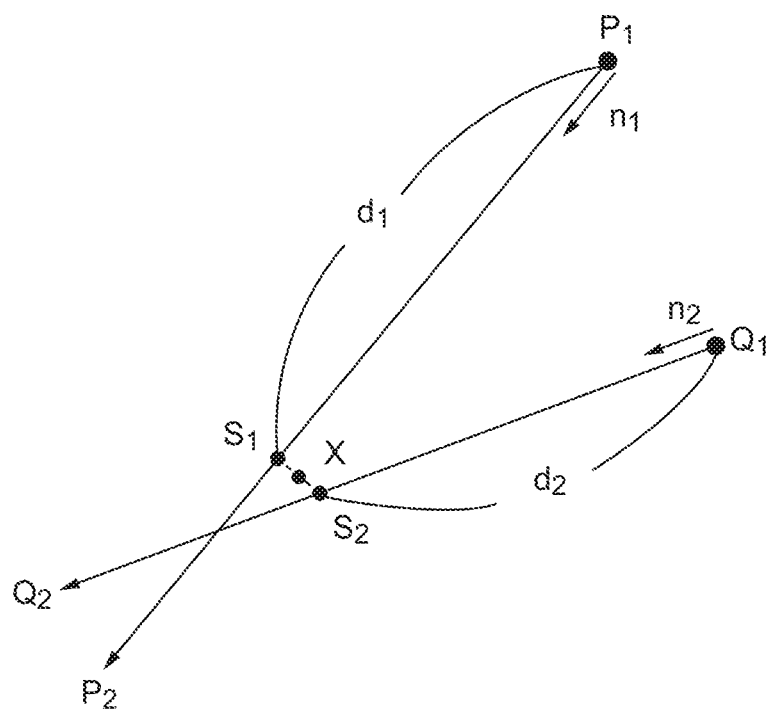
FIG. 18 is a view for explaining a method of calculating the position of an insertion point according to the embodiment.

The other method is to perform the calculation from the posture of a surgical instrument manipulator. As shown in FIG. 18, assume that the rotation centers of a gimbal mechanism in two given postures are $P_1$ and $Q_1$, and the corresponding distal end coordinates of the robot medical instrument 127 are $P_2$ and $Q_2$. Ideally, the rotation centers in these postures are supposed to match. As shown in FIG. 18, however, the rotation centers become twisted positions due to, for example, deflection of the abdominal wall. Therefore, this method uses a point x between these postures as the insertion point (rotation center).

To obtain the coordinates of the insertion point x, points $S_1$ and $S_2$ at which perpendicular lines extending from straight lines intersect each other are calculated in accordance with the following equations:

$$d_1 = \frac{n_1 \cdot PQ_{11} - (n_1 \cdot n_2)(n_2 \cdot PQ_{11})}{1 - (n_1 \cdot n_2)^2} \quad (1)$$

$$d_2 = \frac{(n_1 \cdot n_2)(n_1 \cdot PQ_{11}) - n_2 \cdot PQ_{11}}{1 - (n_1 \cdot n_2)^2}$$

$$S_1 = P_1 + d_1 n_1$$

$$S_2 = Q_1 + d_2 n_2$$

where $n_1$ and $n_2$ represent unit vectors representing the postures of the surgical instrument manipulator, and $PQ_{11}$ represents a vector extending from $P_1$ to $Q_1$.

When the points $S_1$ and $S_2$ are obtained, the point x between them can be obtained by:

$$x = \frac{S_1 + S_2}{2} \quad (2)$$

Even when obtaining the position of the rotation center from a larger number of postures, it is possible to obtain intermediate points by a method similar to the above method, and use the average value as the rotation center.

In step S1711, the control unit 201 calculates the position of the insertion point by using one or both of the above-mentioned calculation methods. Consequently, the control unit 201 can specify the position of the robot-side sheath tube 125 on the spatial coordinate system (robot coordinate system) of the surgery supporting apparatus 200, and can control the motion of each robot arm in accordance with the angle and depth of insertion of the handheld medical instrument into the body cavity.

Note that the insertion point may fluctuate on the robot coordinate system during a surgery due to, for example, a slight motion of the peritoneum of a patient. In this embodiment, however, the robot arm has the 2-axis gimbal mechanism 301 of a passive joint. This makes it possible to follow and detect a slight movement of the insertion point (unlike a robot arm that supports the insertion point by an RCM (Remote Center of Motion) mechanism). When the position of the insertion point fluctuates, the control unit 201 executes the calculation method shown in FIG. 18 at a predetermined time interval in a loop that controls the robot arm by using a handheld surgical instrument. Consequently, a deviation of the insertion point 901 on the robot coordinate system can be corrected. That is, the manipulation accuracy of the distal end portion of the robot medical instrument 127 can be held high.

Note that the position of the operator-side sheath tube 135 can be obtained by a method different from the method of specifying the position of the insertion point of the robot-side sheath tube 125, and can also be obtained by using a robot arm to be inserted into the robot-side sheath tube 125. For example, after each robot arm and the corresponding robot-side sheath tube 125 are initialized, one of the two robot medical instruments 127 is extracted from the allocated sheath tube and inserted into the operator-side sheath tube 135. As a consequence, position information of the operator-side sheath tube 135 on the robot coordinate system can be obtained.

(Semiautomatic Retraction Mode)

As described above, the surgery supporting apparatus 200 is used to assist the operative procedure of an operator by using a robot arm. For example, the use of the surgery supporting apparatus 200 makes it possible to secure an operation field by holding an organ and fixing it in the place by the robot medical instrument 127, perform suturing by causing the robot medical instrument 127 to hold a needle and a thread, or move an endoscope to an intended position.

A semiautomatic retraction mode of the surgery supporting apparatus 200 will be explained below by taking, as an example, a state in which an organ is pulled and fixed by the robot medical instrument 127. An operator performs a treatment (generally, dissection or the like) on an organ. Since, however, the robot medical instrument 127 is spatially kept fixed, the retraction force sometimes weakens when dissection progresses and the shape of the organ changes. A surgery by an operator can be performed more smoothly if the retraction force on an organ can simply be adjusted in accordance with the progress and status of the surgery, in the same manner as when a human performs retraction as an assistant.

In the semiautomatic retraction mode of the surgery supporting apparatus 200, therefore, the retraction force when using the robot medical instrument 127 can simply be adjusted. Note that a case in which an operator uses a switch attached to the handheld medical instrument 131 included in the manipulation unit 202 in order to switch the operation mode of the surgery supporting apparatus 200 to the semiautomatic retraction mode will be explained as an example, but another manipulating means may also be used. Switching is not limited to a physical switch and may also be based on voice recognition or gesture recognition.

First, an operator controls the robot arm by using, for example, a surgical instrument to be used in a treatment, and causes the robot medical instrument 127 to pull an organ. In this case, the control unit 201 temporarily records the locus of the distal end coordinates of the robot medical instrument 127, from the start to the end of the manipulation on the robot medical instrument 127, in the memory 205. Based on the recorded locus, the control unit 201 calculates a direction (called a retraction direction) in which the distal end is moving immediate before the end of the manipulation. However, the retraction direction is not limited to the direction obtained by last sampling, but can also be a direction obtained by integrating or averaging the movement of the distal end position during a predetermined period immediately before the end of the manipulation.

When detecting the manipulation of switching to the semiautomatic manipulation mode, the control unit 201 controls the robot arm such that the distal end coordinates of the robot medical instrument 127 move in only a predetermined direction matching the retraction direction (that is, restricts the movement of the distal end position of the medical instrument 127). More specifically, in a normal operation mode in which the distal end position of the robot medical instrument 127 is controlled by using a surgical instrument, a manipulation must be performed by using a 6-degree-of-freedom positioning surgical instrument. When using the semiautomatic retraction mode, however, the retraction force can be adjusted by performing only a 1-degree-of-freedom manipulation.

The adjustment of the distance and the speed at which the distal end position is moved in the retraction direction in the semiautomatic retraction mode is not limited to the manipulation using a surgical instrument, and it is also possible to use a foot switch or the like of the manipulation unit 202 or add a new switch or the like. For example, in the semiautomatic retraction mode, the control unit 201 can perform control in a direction of increasing the retraction force if it is detected that a surgical instrument held by an operator is rotated clockwise around the shaft, and can perform control in a direction of decreasing the retraction force if it is detected that the surgical instrument is rotated counterclockwise. Another method may also be used as long as the method can change a 1-degree-of-freedom velocity.

In the surgery supporting apparatus according to this embodiment as has been explained above, the posture of the robot medical instrument 127 that is inserted into a body cavity and mechanically drivable can be controlled by using the handheld medical instrument 131 to be inserted into the body cavity. When the operation mode of the surgery supporting apparatus is the robot arm manipulation mode, the motion of the robot arm is controlled in accordance with the posture of the handheld surgical instrument. On the other hand, when the operation mode is the manual manipulation mode, the motion of the robot arm is controlled in accordance with a manual manipulation on the robot arm. This makes it possible to provide a surgery supporting apparatus not requiring a console that is difficult to install in an operating room, and capable of simply manipulating a robot arm. In addition, manipulations can be performed by a minimum number of operators, so the interference between the robot arm and the operators can be reduced.

Furthermore, the frame to which the horizontal robot arm is attached and the forward/backward motion in the vertical direction of the linear-motion robot arm are implemented by the common support member. This can downsize the surgery supporting apparatus and reduce the cost.

Note that the parts of the above-described surgery supporting apparatus can also be implemented as they are separated or integrated. Note also that the present invention can include a case in which a control unit including one or more processors reads out a program of a computer that executes the above-described processing from a storage medium and executes the readout program, and a case in which the program is obtained by wired communication or wireless communication and executed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A surgery supporting apparatus capable of controlling a posture of a first surgical instrument that is inserted into a body cavity and mechanically drivable, by using a second surgical instrument to be inserted into the body cavity, comprising:
    a robot arm configured to control the posture of the first surgical instrument attached to the robot arm, the robot arm having a grip portion to be grasped by an operator and having a first switch arranged on a circumference of the grip portion;
    one or more processors; and
    a memory storing instructions which, when the instructions are executed by the one or more processors, cause the surgery supporting apparatus to:
    switch, among motion modes, a motion mode being for controlling a motion of the robot arm; and
    control the motion of the robot arm in accordance with the motion mode,
    wherein the motion modes include a first mode in which the second surgical instrument is used to control the first surgical instrument, and a second mode in which the robot arm is moved by a manipulation including contact to the robot arm, and
    wherein the instructions cause the surgery supporting apparatus to control the motion of the robot arm such that the posture of the first surgical instrument is controlled in accordance with the posture of the second surgical instrument, in a case where the motion mode is the first mode, and control the motion of the robot arm in accordance with a force added to the robot arm by the manipulation including contact to the robot arm only while the first switch on the circumference of the grip portion is pressed, in a case where the motion mode is the second mode.

2. The surgery supporting apparatus according to claim 1, wherein the motion mode further includes a third mode in which the second surgical instrument is used to perform a treatment.

3. The surgery supporting apparatus according to claim 1, wherein the instructions cause the surgery supporting apparatus to switch the motion mode to the second mode when detecting the manipulation including contact to the robot arm.

4. The surgery supporting apparatus according to claim 1, wherein the second mode includes a release mode in which the robot arm is moved in accordance with a force received by the manipulation including contact to the robot arm, and a vector manipulation mode in which the robot arm is driven in accordance with an instruction input by the manipulation including contact to the robot arm.

5. The surgery supporting apparatus according to claim 4, wherein in a case where the motion mode is the release mode, the instructions cause the surgery supporting apparatus to release at least a part of a driving force to be given to maintain the posture of the robot arm or at least a part of a brake.

6. The surgery supporting apparatus according to claim 4, wherein in a case where the motion mode is the vector manipulation mode, the instructions cause the surgery supporting apparatus to control the motion of the robot arm in accordance with an axial direction of a shaft of the first surgical instrument, and with a direction, which is indicated by the instruction, in the axial direction of the shaft of the first surgical instrument.

7. The surgery supporting apparatus according to claim 1, wherein the robot arm includes a first robot arm including a first arm and at least one second arm, the first arm capable of moving forward and backward in a vertical direction, and the at least one second arm capable of moving by rotation around an axis in the vertical direction.

8. The surgery supporting apparatus according to claim 7, further comprising a first base to which the first arm of the first robot arm is attached such that the first arm moves forward and backward in the vertical direction, and a second base to which the first base is attached such that the first base moves forward and backward in the vertical direction.

9. The surgery supporting apparatus according to claim 7, further comprising a second robot arm including a third arm capable of moving forward and backward in the vertical direction, a fourth arm that moves by rotation around an axis in the vertical direction, and a fifth arm capable of moving forward and backward in an axial direction of the fourth arm.

10. The surgery supporting apparatus according to claim 7, further comprising:
a first base to which the first arm of the first robot arm is attached such that the first arm moves forward and backward in the vertical direction;
a second base to which the first base is attached such that the first base moves forward and backward in the vertical direction; and
a second robot arm including a third arm capable of moving forward and backward in the vertical direction, a fourth arm that moves by rotation around an axis in the vertical direction, and a fifth arm capable of moving forward and backward in an axial direction of the fourth arm,
wherein the first base and the second robot arm are attached, to be movable forward and backward in the vertical direction, to a common support member included in the second base.

11. A surgery supporting apparatus capable of controlling a posture of a first surgical instrument that is inserted into a body cavity and mechanically drivable, by using a second surgical instrument to be inserted into the body cavity, comprising:
a robot arm configured to control the posture of the first surgical instrument attached to the robot arm;
one or more processors; and
a memory storing instructions which, when the instructions are executed by the one or more processors, cause the surgery supporting apparatus to:
switch, among motion modes, a motion mode being for controlling a motion of the robot arm; and
control the motion of the robot arm in accordance with the motion mode,
wherein the motion modes include a first mode in which the second surgical instrument is used to control the first surgical instrument, and a second mode in which the robot arm is moved by a manipulation including contact to the robot arm,
wherein the instructions cause the surgery supporting apparatus to control the motion of the robot arm such that the posture of the first surgical instrument is controlled in accordance with the posture of the second surgical instrument, in a case where the motion mode is the first mode, and control the motion of the robot arm in accordance with the manipulation including contact to the robot arm, in a case where the motion mode is the second mode, and
wherein when detecting a predetermined manipulation in the first mode, the instructions cause the surgery supporting apparatus to control the motion of the robot arm such that a movement of a distal end position of the first surgical instrument is restricted.

12. The surgery supporting apparatus according to claim 11, wherein when detecting the predetermined manipulation, the instructions cause the surgery supporting apparatus to control the motion of the robot arm such that the distal end position of the first surgical instrument moves in only a predetermined direction.

13. The surgery supporting apparatus according to claim 11, wherein the instructions cause the surgery supporting apparatus to control the motion of the robot arm, based on a locus of the distal end position of the first surgical instrument before the movement of the distal end position of the first surgical instrument is restricted.

14. A surgery supporting apparatus capable of controlling a posture of a first surgical instrument that is inserted into a body cavity and mechanically drivable, by using a second surgical instrument to be inserted into the body cavity, comprising:
a robot arm configured to control the posture of the first surgical instrument attached to the robot arm;
one or more processors; and
a memory storing instructions which, when the instructions are executed by the one or more processors, cause the surgery supporting apparatus to:
switch, among motion modes, a motion mode being for controlling a motion of the robot arm; and
control the motion of the robot arm in accordance with the motion mode,
wherein the motion modes include a first mode in which the second surgical instrument is used to control the first surgical instrument, and a second mode in which the robot arm is moved by a manipulation including contact to the robot arm, wherein the instructions cause the surgery supporting apparatus to control the motion of the robot arm such that the posture of the first surgical instrument is controlled in accordance with the posture of the second surgical instrument, in a case where the motion mode is the first mode, and control the motion of the robot arm in accordance with the manipulation including contact to the robot arm, in a case where the motion mode is the second mode, and wherein when detecting that a distal end of the first surgical instrument attached to the robot arm is inserted into a sheath tube inserted into the body cavity while the motion mode is the second mode, the instructions cause the surgery supporting apparatus to associate the robot arm with the sheath tube.

15. A surgery supporting apparatus capable of controlling a posture of a first surgical instrument that is inserted into a body cavity and mechanically drivable, by using a second surgical instrument to be inserted into the body cavity, comprising:
- a robot arm configured to control the posture of the first surgical instrument attached to the robot arm;
- one or more processors; and
- a memory storing instructions which, when the instructions are executed by the one or more processors, cause the surgery supporting apparatus to:
- switch, among motion modes, a motion mode being for controlling a motion of the robot arm; and
- control the motion of the robot arm in accordance with the motion mode,
- wherein the motion modes include a first mode in which the second surgical instrument is used to control the first surgical instrument, and a second mode in which the robot arm is moved by a manipulation including contact to the robot arm,
- wherein the instructions cause the surgery supporting apparatus to control the motion of the robot arm such that the posture of the first surgical instrument is controlled in accordance with the posture of the second surgical instrument, in a case where the motion mode is the first mode, and control the motion of the robot arm in accordance with the manipulation including contact to the robot arm, in a case where the motion mode is the second mode, and
- wherein when detecting that a distal end of the first surgical instrument attached to the robot arm is inserted into a sheath tube inserted into the body cavity while the motion mode is the second mode, the instructions cause the surgery supporting apparatus to calculate a position of a reference point of an angle and a depth of insertion, into the body cavity, of a shaft of the first surgical instrument.

16. A surgery supporting apparatus capable of controlling a posture of a first surgical instrument that is inserted into a body cavity and mechanically drivable, by using a second surgical instrument to be inserted into the body cavity, comprising:
- a robot arm configured to control the posture of the first surgical instrument attached to the robot arm;
- one or more processors; and
- a memory storing instructions which, when the instructions are executed by the one or more processors, cause the surgery supporting apparatus to:
- switch, among motion modes, a motion mode being for controlling a motion of the robot arm; and
- control the motion of the robot arm in accordance with the motion mode,
- wherein the motion modes include a first mode in which the second surgical instrument is used to control the first surgical instrument, and a second mode in which the robot arm is moved by a manipulation including contact to the robot arm,
- wherein the instructions cause the surgery supporting apparatus to control the motion of the robot arm such that the posture of the first surgical instrument is controlled in accordance with the posture of the second surgical instrument, in a case where the motion mode is the first mode, and control the motion of the robot arm in accordance with the manipulation including contact to the robot arm, in a case where the motion mode is the second mode, and
- wherein the instructions cause the surgery supporting apparatus to calculate a position of a reference point of an angle and a depth of insertion, into the body cavity, of a shaft of the first surgical instrument, based on a plurality of postures of the first surgical instrument obtained when the shaft of the first surgical instrument is inserted into the body cavity at different angles.

17. The surgery supporting apparatus according to claim 16, wherein in a case where the motion mode is the first mode, the instructions cause the surgery supporting apparatus to calculate the position of the reference point at predetermined time intervals, based on the plurality of postures of the first surgical instrument.

18. A control method of a surgery supporting apparatus capable of controlling a posture of a first surgical instrument that is inserted into a body cavity and mechanically drivable, by using a second surgical instrument to be inserted into the body cavity, the surgery supporting apparatus including a robot arm configured to control the posture of the first surgical instrument attached to the robot arm, the robot arm having a grip portion to be grasped by an operator and having a first switch arranged on a circumference of the grip portion, and the control method comprising:
- switching, among motion modes, a motion mode being for controlling a motion of the robot arm; and
- controlling the motion of the robot arm in accordance with the motion mode,
- wherein the motion modes include a first mode in which the second surgical instrument is used to control the first surgical instrument, and a second mode in which the robot arm is moved by a manipulation including contact to the robot arm, and
- in the controlling, the motion of the robot arm is controlled such that the posture of the first surgical instrument is controlled in accordance with a posture of the second surgical instrument, in a case where the motion mode is the first mode, and the motion of the robot arm is controlled in accordance with a force added to the robot arm by the manipulation including contact to the robot arm only while the first switch on the circumference of the grip portion is pressed, in a case where the motion mode is the second mode.

19. A non-transitory computer-readable storage medium storing a program for causing a computer to execute a control method of a surgery supporting apparatus capable of controlling a posture of a first surgical instrument that is inserted into a body cavity and mechanically drivable, by using a second surgical instrument to be inserted into the body cavity, the surgery supporting apparatus including a robot arm configured to control the posture of the first surgical instrument attached to the robot arm, the robot arm having a grip portion to be grasped by an operator and having a first switch arranged on a circumference of the grip portion, and the control method comprising:
switching, among motion modes, a motion mode being for controlling a motion of the robot arm; and
controlling the motion of the robot arm in accordance with the motion mode,
wherein the motion modes include a first mode in which the second surgical instrument is used to control the first surgical instrument, and a second mode in which the robot arm is moved by a manipulation including contact to the robot arm, and
in the controlling, the motion of the robot arm is controlled such that the posture of the first surgical instrument is controlled in accordance with the posture of the second surgical instrument, in a case where the motion mode is the first mode, and the motion of the robot arm is controlled in accordance with a force added to the robot arm by the manipulation including contact to the robot arm only while the first switch on the circumference of the grip portion is pressed, in a case where the motion mode is the second mode.

20. The surgery supporting apparatus according to claim 4, further comprising a second switch provided on the robot arm to manipulate the robot arm, wherein the instructions cause the surgery supporting apparatus to control the motion of the robot arm in accordance with the instruction input to the second switch by the manipulation including contact to the second switch in the vector manipulation mode.

21. The surgery supporting apparatus according to claim 1, wherein the instructions cause the surgery supporting apparatus to release a brake for maintaining the posture of the robot arm only while the first switch on the circumference of the grip portion is pressed, in a case where the motion mode is the second mode.

22. The surgery supporting apparatus according to claim 1, wherein the first switch includes a plurality of switches, the plurality of switches being arranged on the circumference of the grip portion.

* * * * *